(12) United States Patent
Wang et al.

(10) Patent No.: US 9,099,654 B2
(45) Date of Patent: Aug. 4, 2015

(54) BENZOFLUORENE COMPOUND, EMISSION MATERIALS AND ORGANIC ELECTROLUMINESCENT DEVICE

(71) Applicant: JNC Corporation, Tokyo (JP)

(72) Inventors: Guofang Wang, Chiba (JP); Akiko Kageyama, Chiba (JP); Toshihiro Koike, Chiba (JP); Manabu Uchida, Chiba (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 13/747,605

(22) Filed: Jan. 23, 2013

(65) Prior Publication Data
US 2013/0134405 A1 May 30, 2013

Related U.S. Application Data

(62) Division of application No. 11/905,737, filed on Oct. 3, 2007, now abandoned.

(30) Foreign Application Priority Data

Oct. 5, 2006 (JP) .................................. 2006-273809
Apr. 27, 2007 (JP) .................................. 2007-118535

(51) Int. Cl.
 H01L 51/50 (2006.01)
 C07C 13/66 (2006.01)
(Continued)

(52) U.S. Cl.
 CPC ............ *H01L 51/0039* (2013.01); *C07C 13/66* (2013.01); *C09K 11/06* (2013.01);
(Continued)

(58) Field of Classification Search
 CPC  C07C 13/66; C07C 2101/14; C07C 2103/26; C07C 2103/40; C09K 11/06; C09K 2211/1007; C09K 2211/1011; H01L 51/0039; H01L 51/0054; H01L 51/0058; H01L 51/006; H01L 51/0071; H01L 51/0072; H01L 51/0081; H01L 51/0094; H05B 33/14; Y10T 428/31504
See application file for complete search history.

(56) References Cited

U.S. PATENT DOCUMENTS 6,468,675 B1 10/2002 Ishikawa et al.
6,686,065 B2 2/2004 Chen
(Continued)

FOREIGN PATENT DOCUMENTS

WO   03/051092   6/2003
WO   2004/061047  7/2004
(Continued)

OTHER PUBLICATIONS

Ken-Tsung Wong et al., "Synthesis and Properties of 9,9-Diarylfluorene-Based Triaryldiamines", *Organic Letters*, vol. 3, No. 15, pp. 2285-2288, 2001.
(Continued)

*Primary Examiner* — Dawn Garrett
(74) *Attorney, Agent, or Firm* — Wenderoth, Lind & Ponack, L.L.P.

(57) ABSTRACT

Disclosed are benzofluorene compounds of formula (1) exhibiting excellent performance when applied to an organic electroluminescent device,

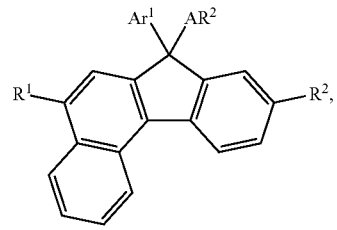

(1)

wherein $Ar^1$ and $Ar^2$ are aryl which may be substituted; $R^1$ and $R^2$ each are independently hydrogen, alkyl which may be substituted, cycloalkyl which may be substituted or aryl which may be substituted, and at least one of $R^1$ and $R^2$ is aryl which may be substituted; and the substituents in $Ar^1$, $Ar^2$, $R^1$ and $R^2$ each are independently selected from the group consisting of alkyl having 1 to 24 carbon atoms, cycloalkyl having 3 to 12 carbon atoms and aryl having 6 to 30 carbon atoms.

19 Claims, 1 Drawing Sheet

(51) Int. Cl.
*H01L 51/00* (2006.01)
*C09K 11/06* (2006.01)
*H05B 33/14* (2006.01)

(52) U.S. Cl.
CPC ......... *H01L 51/006* (2013.01); *H01L 51/0054* (2013.01); *H05B 33/14* (2013.01); *C07C 2101/14* (2013.01); *C07C 2103/26* (2013.01); *C07C 2103/40* (2013.01); *C09K 2211/1007* (2013.01); *C09K 2211/1011* (2013.01); *H01L 51/0058* (2013.01); *H01L 51/0071* (2013.01); *H01L 51/0072* (2013.01); *H01L 51/0081* (2013.01); *H01L 51/0094* (2013.01); *Y10T 428/31504* (2015.04)

(56) References Cited

U.S. PATENT DOCUMENTS

| | | | |
|---|---|---|---|
| 6,849,348 | B2 | 2/2005 | Zheng et al. |
| 7,919,773 | B2 | 4/2011 | Kawakami et al. |
| 2002/0168543 | A1 | 11/2002 | Ishikawa et al. |
| 2003/0118866 | A1 | 6/2003 | Oh et al. |
| 2003/0143422 | A1 | 7/2003 | Chen |
| 2004/0076853 | A1* | 4/2004 | Jarikov ................. 428/690 |
| 2004/0131880 | A1 | 7/2004 | Zheng et al. |
| 2004/0131881 | A1 | 7/2004 | Zheng et al. |
| 2004/0241496 | A1 | 12/2004 | Zheng et al. |
| 2005/0202279 | A1 | 9/2005 | Zheng et al. |
| 2008/0160348 | A1 | 7/2008 | Smith |
| 2008/0233429 | A1* | 9/2008 | Oguma et al. ................ 428/690 |
| 2010/0164370 | A1* | 7/2010 | Noguchi ..................... 313/504 |

FOREIGN PATENT DOCUMENTS

| | | | |
|---|---|---|---|
| WO | 2004/061048 | | 7/2004 |
| WO | WO 2005/056633 | * | 6/2005 |

OTHER PUBLICATIONS

Office Action issued Sep. 11, 2012 in corresponding Japanese Application No. 2007-258601.
Korean Office Action issued Dec. 24, 2013 in corresponding Korean Application No. 10-2007-0099943.
Korean Office Action issued Jun. 27, 2014 in corresponding Korean Patent Application No. 10-2007-0099943.
Korean Office Action issued Dec. 2, 2014 in corresponding Korean Patent Application No. 10-2007-0099943.
Korean Office Action issued Feb. 26, 2015 in corresponding Korean Patent Application No. 10-2014-0130488.

\* cited by examiner

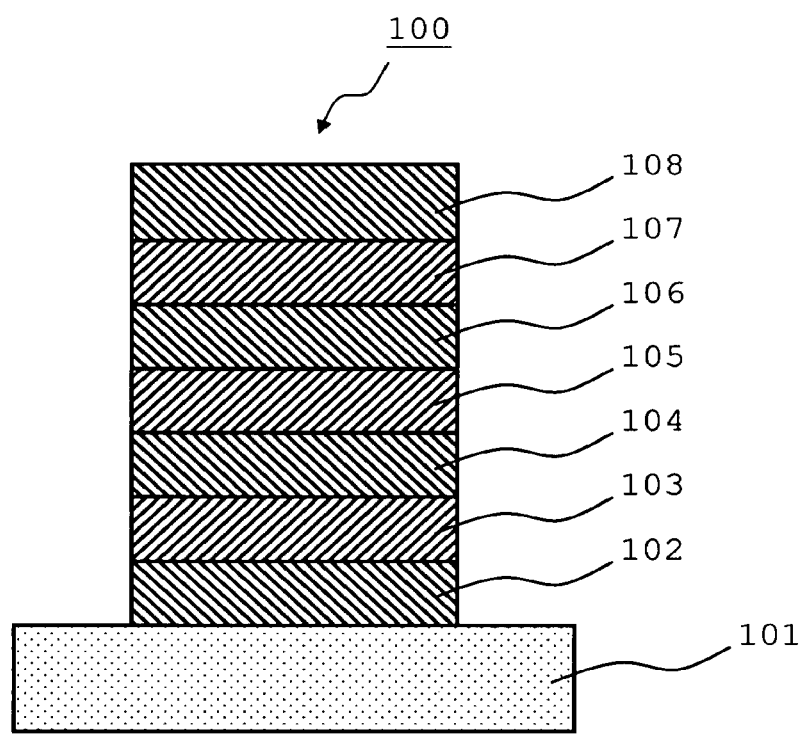

BENZOFLUORENE COMPOUND, EMISSION MATERIALS AND ORGANIC ELECTROLUMINESCENT DEVICE

FIELD OF THE INVENTION

The present invention relates to a benzofluorene compound, a material for an emission layer using the compound and an organic electroluminescent device.

BACKGROUND OF THE INVENTION

An organic electroluminescent device is a light emitting device which is a spontaneous emission type and is expected as a light emitting device for display or lighting. A display unit using an electroluminescent light emitting device has so far been researched in various cases because of possibility of small power consumption and reduction in a thickness. Further, an organic electroluminescent device comprising organic materials has so far been actively investigated since reduction in a weight and increase in a size are easy. In particular, developments of organic materials having light emitting characteristics including a blue color which is one of three primary colors and developments of organic materials endowed with charge transport ability (having possibility of being derived into semiconductors and superconductors) of holes and electrons have so far been actively researched regardless of high molecular compounds and low molecular compounds.

An organic electroluminescent device has a structure comprising a pair of electrodes comprising an anode and a cathode and a single layer or plural layers which are disposed between a pair of the electrodes and which contain organic compounds. The layer containing organic compounds includes an emission layer and a charge transport/injection layer which transports or injects charges such as a hole and an electron, and various organic materials have been developed as the organic compounds (for example, International Publication No. 2004/061047 pamphlet and International Publication No. 2004/061048 pamphlet (JP H18-512395 (through PCT) A/2006): refer to a patent document 1 and a patent document 2). However, only high molecular compounds of benzofluorene are disclosed in the examples of the patent documents. Also, International Publication No. 2003/051092 pamphlet (JP H17-513713 (through PCT) A/2005), for example, describes dibenzofluorene compounds having amino substituted with aryls (refer to a patent document 3). However, the document describes only structural formulas thereof, and does not describe the specific characteristics thereof.

Patent document 1: International Publication No. 2004/061047 pamphlet
Patent document 2: International Publication No. 2004/061048 pamphlet (JP H18-512395 (through PCT) A/2006)
Patent document 3: International Publication No. 2003/051092 pamphlet (JP H17-513713 (through PCT) A/2005)

However, even if the organic materials described above are used, organic electroluminescent devices having satisfactory performances in terms of heat resistance, luminous efficiency, current efficiency, device life and external quantum efficiency have not yet been obtained. Under the situation described above, desired to be developed is an organic electroluminescent device having further better performances in terms of heat resistance, luminous efficiency, current efficiency, device life and external quantum efficiency, that is, a compound which can provide the device.

Further, in order to meet commercial production of light emitting devices, desired are organic materials which are more easily synthesized and organic materials which can accept any processing conditions in applying to devices. For example, organic materials having an excellent solubility in a solvent are relatively easily synthesized and have the merit that they are not limited to a vapor deposition method in forming layers.

SUMMARY OF THE INVENTION

Intensive investigations repeated by the present inventors in order to solve the problems described above have resulted in successfully producing a benzofluorene compound represented by Formula (1) shown below. Further, the present inventors have found that an organic electroluminescent device which is improved in luminous efficiency, current efficiency, device life and external quantum efficiency is obtained by disposing a layer containing the benzofluorene compound between a pair of electrodes to constitute the organic electroluminescent device, and thus they have completed the present invention.

That is, the present invention provides the following benzofluorene compound.

[1] A benzofluorene compound represented by the following Formula (1):

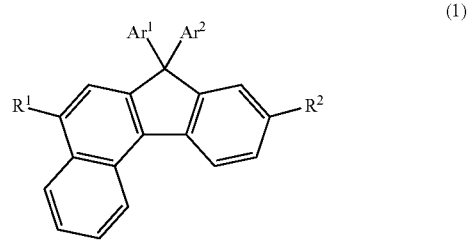

(wherein $Ar^1$ and $Ar^2$ are aryl which may be substituted; $R^1$ and $R^2$ each are independently hydrogen, alkyl which may be substituted, cycloalkyl which may be substituted or aryl which may be substituted, and at least one of $R^1$ and $R^2$ is aryl which may be substituted).

[2] The benzofluorene compound as described in [1], wherein $Ar^1$ and $Ar^2$ are aryl having 6 to 30 carbon atoms which may be substituted;
$R^1$ and $R^2$ each are independently hydrogen, alkyl having 1 to 24 carbon atoms which may be substituted, cycloalkyl having 3 to 12 carbon atoms which may be substituted or aryl having 6 to 30 carbon atoms which may be substituted, and at least one of $R^1$ and $R^2$ is aryl having 6 to 30 carbon atoms which may be substituted; and
substituents in $Ar^1$, $Ar^2$, $R^1$ and $R^2$ each are independently alkyl having 1 to 24 carbon atoms, cycloalkyl having 3 to 12 carbon atoms or aryl having 6 to 30 carbon atoms.

[3] The benzofluorene compound as described in [1], wherein $Ar^1$ and $Ar^2$ are aryl having 6 to 16 carbon atoms which may be substituted;
$R^1$ and $R^2$ are aryl having 6 to 24 carbon atoms which may be substituted; and
substituents in $Ar^1$, $Ar^2$, $R^1$ and $R^2$ each are independently alkyl having 1 to 12 carbon atoms, cycloalkyl having 3 to 6 carbon atoms or aryl having 6 to 20 carbon atoms.

[4] The benzofluorene compound as described in [1], wherein $Ar^1$ and $Ar^2$ are aryl having 6 to 12 carbon atoms which may be substituted;
$R^1$ and $R^2$ are aryl having 6 to 20 carbon atoms which may be substituted; and substituents in Ar¹, Ar², R¹ and R² each are independently methyl, ethyl, propyl, t-butyl, cyclobutyl, cyclopentyl, cyclohexyl, phenyl, biphenylyl or naphthyl.

[5] The benzofluorene compound as described in [1], wherein Ar¹ and Ar² each are independently phenyl or biphenylyl; and
R¹ and R² each are independently phenyl, biphenylyl, terphenylyl, quaterphenylyl, naphthyl or phenanthryl.

[6] The benzofluorene compound as described in [1], wherein Ar¹ and Ar² are aryl having 6 to 16 carbon atoms which may be substituted;
one of R¹ and R² is hydrogen, and the other is aryl having 6 to 24 carbon atoms which may be substituted; and
substituents in Ar¹, Ar², R¹ and R² each are independently alkyl having 1 to 12 carbon atoms, cycloalkyl having 3 to 6 carbon atoms or aryl having 6 to 20 carbon atoms.

[7] The benzofluorene compound as described in [1], wherein Ar¹ and Ar² are aryl having 6 to 12 carbon atoms which may be substituted;
one of R¹ and R² is hydrogen, and the other is aryl having 6 to 20 carbon atoms which may be substituted; and
substituents in Ar¹, Ar², R¹ and R² each are independently methyl, ethyl, propyl, t-butyl, cyclobutyl, cyclopentyl, cyclohexyl, phenyl, biphenylyl or naphthyl.

[8] The benzofluorene compound as described in [1], wherein Ar¹ and Ar² each are independently phenyl or biphenylyl; and
one of R¹ and R² is hydrogen, and the other is phenyl, biphenylyl, terphenylyl, quaterphenylyl, naphthyl or phenanthryl.

[9] The benzofluorene compound as described in [1], wherein Ar¹ and Ar² are phenyl;
R¹ is 4-biphenylyl, and R² is 4-biphenylyl.

[10] The benzofluorene compound as described in [1], wherein Ar¹ and Ar² are phenyl;
R¹ is 2-naphthyl, and R² is 2-naphthyl.

[11] The benzofluorene compound as described in [1], wherein Ar¹ and Ar² are phenyl;
R¹ is 4-biphenylyl, and R² is 2-naphthyl.

[12] The benzofluorene compound as described in [1], wherein Ar¹ and Ar² are phenyl;
R¹ is 2-naphthyl, and R² is 4-biphenylyl.

[13] A benzofluorene compound represented by the following Formula (1'):

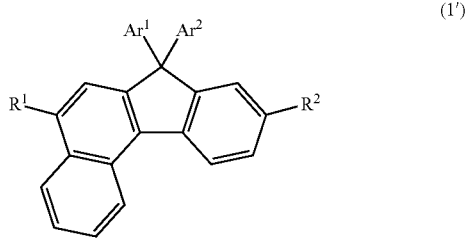

(1')

(wherein Ar¹ and Ar² are aryl which may be substituted;
R¹ is diarylamino having aryl which may be substituted; and
R² is hydrogen, alkyl which may be substituted, cycloalkyl which may be substituted, aryl which may be substituted or diarylamino having aryl which may be substituted).

[14] The benzofluorene compound as described in [13], wherein Ar¹ and Ar² are aryl having 6 to 30 carbon atoms which may be substituted;
R¹ is diarylamino having aryl having 6 to 30 carbon atoms which may be substituted;
R² is hydrogen, alkyl having 1 to 24 carbon atoms which may be substituted, cycloalkyl having 3 to 12 carbon atoms which may be substituted, aryl having 6 to 30 carbon atoms which may be substituted or diarylamino having aryl having 6 to 30 carbon atoms which may be substituted; and
substituents in Ar¹, Ar², R¹ and R² each are independently alkyl having 1 to 24 carbon atoms, aryl having 6 to 30 carbon atoms or heteroaryl having 2 to 30 carbon atoms.

[15] The benzofluorene compound as described in [13], wherein Ar¹ and Ar² are aryl having 6 to 16 carbon atoms which may be substituted;
R¹ is diarylamino having aryl having 6 to 16 carbon atoms which may be substituted;
R² is hydrogen, aryl having 6 to 24 carbon atoms which may be substituted or diarylamino having aryl having 6 to 16 carbon atoms which may be substituted; and
substituents in Ar¹, Ar², R¹ and R² each are independently alkyl having 1 to 12 carbon atoms, aryl having 6 to 12 carbon atoms or heteroaryl having 2 to 10 carbon atoms.

[16] The benzofluorene compound as described in [13], wherein Ar¹ and Ar² are aryl having 6 to 12 carbon atoms which may be substituted;
R¹ is diarylamino having aryl having 6 to 12 carbon atoms which may be substituted;
R² is hydrogen, aryl having 6 to 20 carbon atoms which may be substituted or diarylamino having aryl having 6 to 12 carbon atoms which may be substituted; and
substituents in Ar¹, Ar², R¹ and R² each are independently methyl, ethyl, propyl, t-butyl, phenyl, biphenylyl, naphthyl, pyridyl or thienyl.

[17] The benzofluorene compound as described in [13], wherein Ar¹ and Ar² each are independently phenyl or biphenylyl;
R¹ is diphenylamino, dibiphenylamino, dinaphthylamino or phenylnaphthylamino; and
R² is phenyl, biphenylyl, terphenylyl, quaterphenylyl, naphthyl, phenanthryl, diphenylamino, dibiphenylamino, dinaphthylamino or phenylnaphthylamino.

[18] The benzofluorene compound as described in [13], wherein Ar¹ and Ar² are phenyl; and R¹ and R² are diphenylamino.

[19] A material for an emission layer in a light emitting device and which contains the benzofluorene compound as described in any of [1] to [18].

[20] The material for an emission layer as described in [19], further containing at least one selected from the group consisting of perylene derivatives, borane derivatives, amine-containing styryl derivatives, aromatic amine derivatives, coumarin derivatives, pyran derivatives, iridium complexes and platinum complexes.

[21] An organic electroluminescent device comprising a pair of electrodes comprising an anode and a cathode and an emission layer which is disposed between a pair of the electrodes and which contains the material for an emission layer as described in [19] or [20].

[22] The organic electroluminescent device as described in [21], further comprising an electron transport layer and/or an electron injection layer disposed between the cathode and the emission layer, wherein at least one of the electron transport layer and electron injection layer contains at least one selected from the group consisting of quinolinol metal complexes, pyridine derivatives and phenanthroline derivatives.

[23] The organic electroluminescent device as described in [21], further comprising an electron transport layer and/or an electron injection layer disposed between the cathode and the emission layer, wherein at least one of the electron transport layer and electron injection layer contains quinolinol metal complexes.

[24] The organic electroluminescent device as described in [21], further comprising an electron transport layer and/or an electron injection layer disposed between the cathode and the emission layer, wherein at least one of the electron transport layer and electron injection layer contains pyridine derivatives.

[25] The organic electroluminescent device as described in [21], further comprising an electron transport layer and/or an electron injection layer disposed between the cathode and the emission layer, wherein at least one of the electron transport layer and electron injection layer contains phenanthroline derivatives.

[26] A display unit comprising the organic electroluminescent device as described in any of [21] to [25].

[27] A lighting instrument comprising the organic electroluminescent device as described in any of [21] to [25].

According to the preferred embodiment of the present invention, for example, a benzofluorene compound having excellent characteristics as a material for an emission layer can be provided. Also, an organic electroluminescent device which is improved in heat resistance, luminous efficiency, current efficiency, device life and external quantum efficiency can be provided. Further, the benzofluorene compound according to the preferred embodiment of the present invention is an organic material having an excellent solubility in a solvent and therefore is relatively readily synthesized, and it has the merit that it is not limited to a vapor deposition method in forming layers. As a result thereof, a material for a light emitting device which is suited to commercial production of light emitting devices can be provided.

DETAILED DESCRIPTION OF THE INVENTION

The benzofluorene compound of the present invention shall be explained in details.

The benzofluorene compound according to the present invention is the benzofluorene compound represented by Formula (1) described above.

1. Benzofluorene Compound Represented by Formula (1)

First, the benzofluorene compound represented by Formula (1) shall be explained.

"Aryl" of "aryl which may be substituted" in $Ar^1$, $Ar^2$, $R^1$ and $R^2$ of Formula (1) includes, for example, aryl having 6 to 30 carbon atoms. "Aryl" in $Ar^1$ and $Ar^2$ is preferably aryl having 6 to 16 carbon atoms, more preferably aryl having 6 to 12 carbon atoms. "Aryl" in $R^1$ and $R^2$ is preferably aryl having 6 to 24 carbon atoms, more preferably aryl having 6 to 20 carbon atoms and further preferably aryl having 6 to 12 carbon atoms.

The specific "aryl" includes phenyl, (o-, m- or p-)tolyl, (2,3-, 2,4-, 2,5-, 2,6-, 3,4- or 3,5-)xylyl, mesityl and (o-, m- or p-)cumenyl which are monocyclic aryls, (2-, 3- or 4-)biphenylyl which is dicyclic aryl, (1- or 2-)naphthyl which is condensed dicyclic aryl, terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl and p-terphenyl-4-yl) which are tricyclic aryls, acenaphthylene-(1-, 3-, 4- or 5-)yl, fluorene-(1-, 2-, 3-, 4- or 9-)yl, phenalene-(1- or 2-)yl and (1-, 2-, 3-, 4- or 9-) phenanthryl which are condensed tricyclic aryls, quaterphenylyl (5'-phenyl-m-terphenyl-2-yl, 5'-phenyl-m-terphenyl-3-yl, 5'-phenyl-m-terphenyl-4-yl and m-quaterphenylyl) which are tetracyclic aryls, triphenylene-(1- or 2-)yl, pyrene-(1-, 2- or 4-)yl and naphthacene-(1-, 2- or 5-)yl which are condensed tetracyclic aryls, perylene-(1-, 2- or 3-)yl and pentacene-(1-, 2-, 5- or 6-)yl which are condensed pentacyclic aryls and the like.

The particularly preferred "aryl" in $Ar^1$ and $Ar^2$ is phenyl and 4-biphenylyl. $Ar^1$ and $Ar^2$ may be the same or different, and $Ar^1$ and $Ar^2$ are preferably the same. If $Ar^1$ and $Ar^2$ are aryl, the benzofluorene compound represented by Formula (1) is characterized by that it is increased in rigidity and excellent in heat resistance and that it is extended in life.

The particularly preferred "aryl" in $R^1$ and $R^2$ is phenyl, biphenylyl, terphenylyl, quaterphenylyl, naphthyl and phenanthryl, and among them, phenyl, 4-biphenylyl, 1-naphthyl and 2-naphthyl are preferred. $R^1$ and $R^2$ may be the same or different, and $R^1$ and $R^2$ are preferably the same. If $R^1$ and $R^2$ are aryl, the benzofluorene compound represented by Formula (1) is characterized by that it is excellent in heat resistance, luminous efficiency and life.

"Alkyl" of "alkyl which may be substituted" in $R^1$ and $R^2$ of Formula (1) may be either linear or branched and includes, for example, linear alkyl having 1 to 24 carbon atoms or branched alkyl having 3 to 24 carbon atoms. The preferred "alkyl" is alkyl having 1 to 18 carbon atoms (branched alkyl having 3 to 18 carbon atoms). More preferred "alkyl" is alkyl having 1 to 12 carbon atoms (branched alkyl having 3 to 12 carbon atoms). Further preferred "alkyl" is alkyl having 1 to 6 carbon atoms (branched alkyl having 3 to 6 carbon atoms). Particularly preferred "alkyl" is alkyl having 1 to 4 carbon atoms (branched alkyl having 3 to 4 carbon atoms).

The specific "alkyl" includes methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, n-eicosyl and the like.

"Cycloalkyl" of "cycloalkyl which may be substituted" in $R^1$ and $R^2$ of Formula (1) includes, for example, cycloalkyl having 3 to 12 carbon atoms. The preferred "cycloalkyl" is cycloalkyl having 3 to 10 carbon atoms. More preferred "cycloalkyl" is cycloalkyl having 3 to 8 carbon atoms. Further preferred "cycloalkyl" is cycloalkyl having 3 to 6 carbon atoms.

The specific "cycloalkyl" includes cyclopropyl, cyclobutyl, cyclopentyl, cyclohexyl, methylcyclopentyl, cycloheptyl, methylcyclohexyl, cyclooctyl, dimethylcyclohexyl and the like.

The "substituents" in $Ar^1$, $Ar^2$, $R^1$ and $R^2$ of Formula (1) include alkyl, cycloalkyl and aryl, and the preferred groups thereof include the same groups as the groups explained in the column of the "alkyl" in $R^1$ and $R^2$, the groups explained in the column of the "cycloalkyl" in $R^1$ and $R^2$ and the groups explained in the column of the "aryl" in $Ar^1$, $Ar^2$, $R^1$ and $R^2$.

The "substituents" in $Ar^1$, $Ar^2$, $R^1$ and $R^2$ include, to be specific, alkyl such as methyl, ethyl, n-propyl, isopropyl, n-butyl, isobutyl, s-butyl, t-butyl, n-pentyl, isopentyl, neopentyl, t-pentyl, n-hexyl, n-heptyl, n-octyl, t-octyl, n-nonyl, n-decyl, n-undecyl, n-dodecyl, n-tridecyl, n-tetradecyl, n-pentadecyl, n-hexadecyl, n-heptadecyl, n-octadecyl and the like; cycloalkyl such as cyclopropyl, cyclobutyl, cyclopentyl, cyclohexyl, cycloheptyl, cyclooctyl and the like; aryl such as phenyl, biphenylyl, naphthyl, terphenylyl, phenanthryl and the like; and alkylaryl such as methylphenyl, ethylphenyl, s-butylphenyl, t-butylphenyl, 1-methylnaphthyl, 2-methylnaphthyl, 1,6-dimethylnaphthyl, 2,6-dimethylnaphthyl, 4-t-butylnaphthyl and the like. The number of the substituents is, for example, a maximum substitutable number, and it is preferably 0 to 3, more preferably 0 to 2 and further preferably 0 (non-substituted).

The specific examples of the compound represented by Formula (1) described above include, for example, compounds represented by the following Formulas (1-1) to (1-86). Among the compounds shown below, particularly preferred are the compounds represented by the following Formula (1-1), Formula (1-3), Formula (1-4), Formula (1-7), Formula (1-12), Formula (1-13), Formula (1-14), Formula (1-19), Formula (1-23), Formula (1-24), Formula (1-29), Formula (1-31), Formula (1-33), Formula (1-34), Formula (1-41), Formula (1-43), Formula (1-44), Formula (1-49), Formula (1-51), Formula (1-53), Formula (1-54), Formula (1-59), Formula (1-61), Formula (1-63), Formula (1-64), Formula (1-65), Formula (1-84) and Formula (1-86). Further, more preferred are the compounds represented by the following Formula (1-1), Formula (1-4), Formula (1-7), Formula (1-12), Formula (1-13), Formula (1-14), Formula (1-24), Formula (1-29), Formula (1-31), Formula (1-34), Formula (1-44), Formula (1-59), Formula (1-61), Formula (1-63) and Formula (1-65).

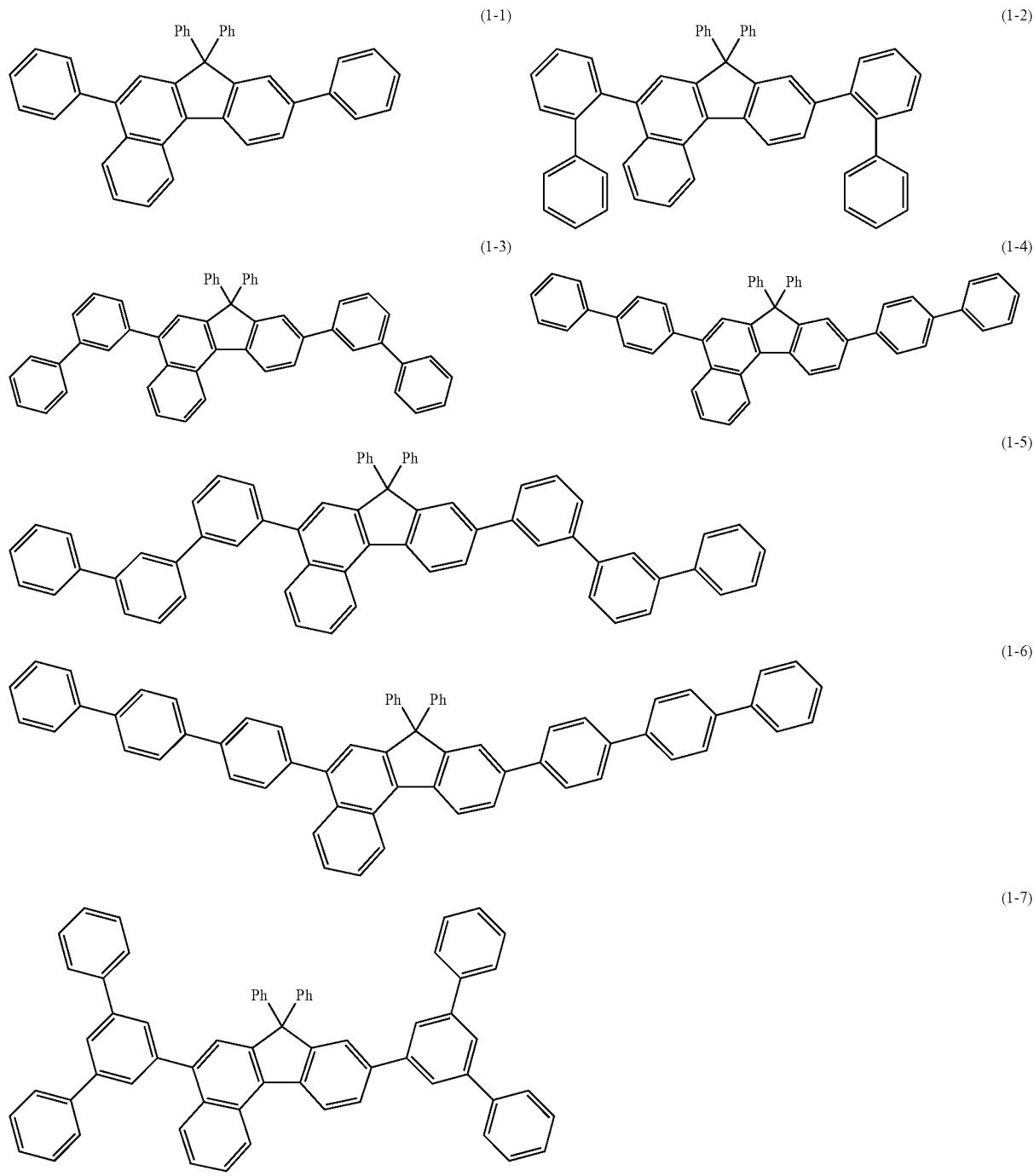

-continued
(1-8)
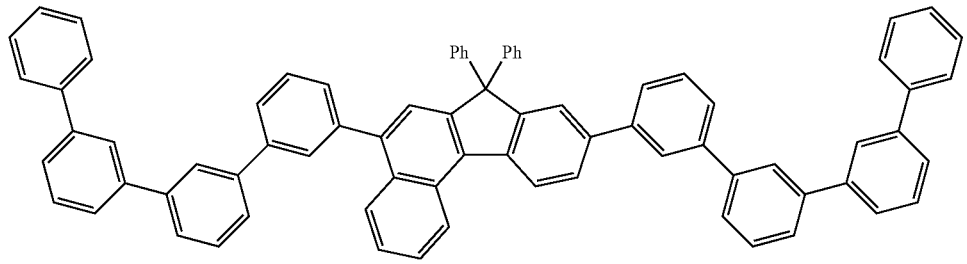
(1-9)
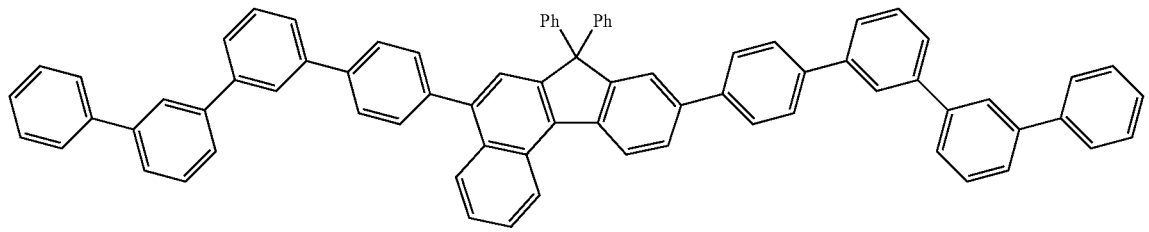
(1-10)
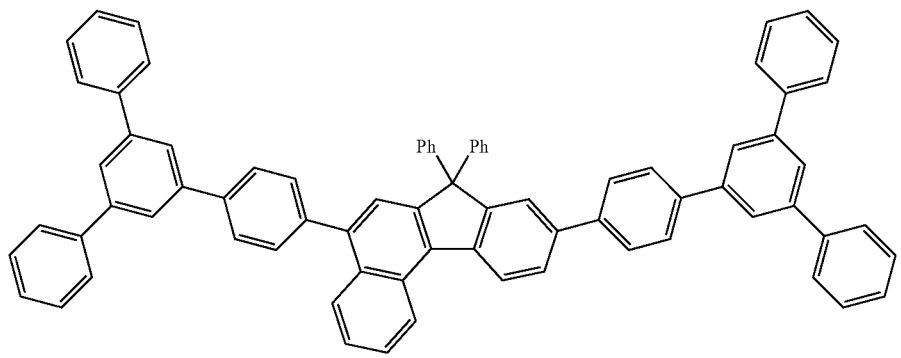
(1-11)
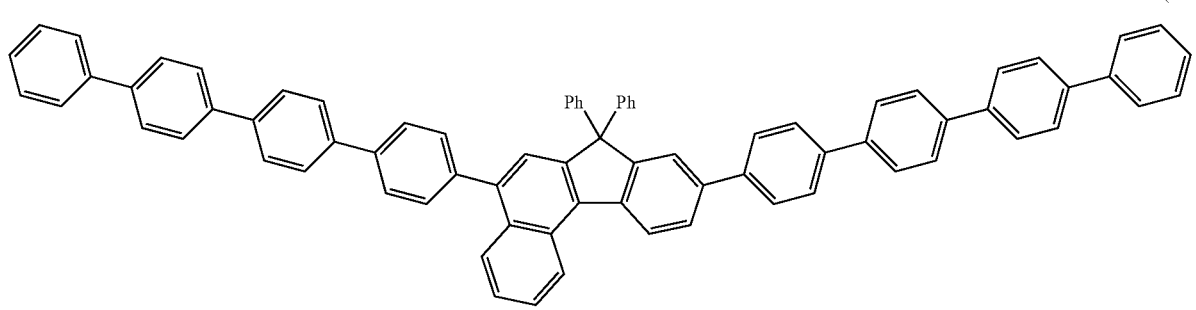
(1-12)
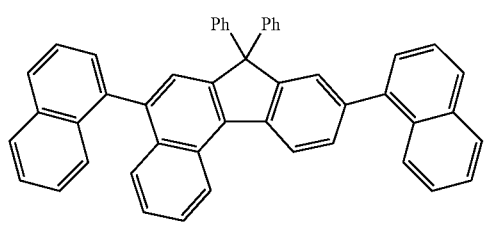
(1-13)
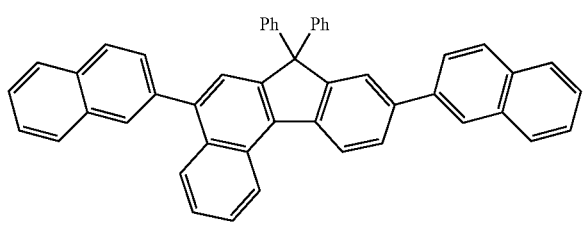
(1-14)
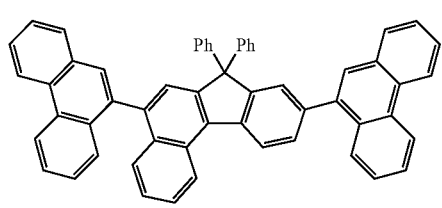
(1-15)
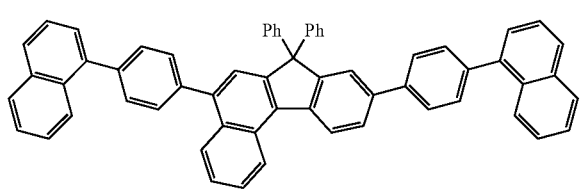

-continued
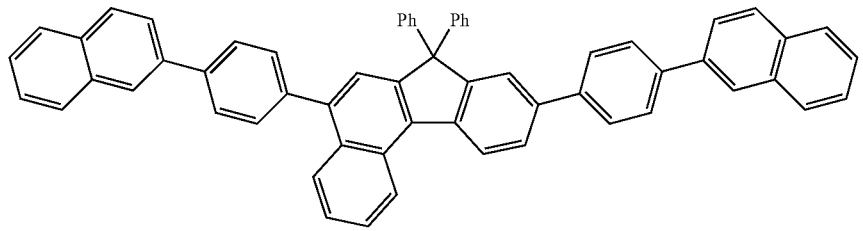
(1-16)
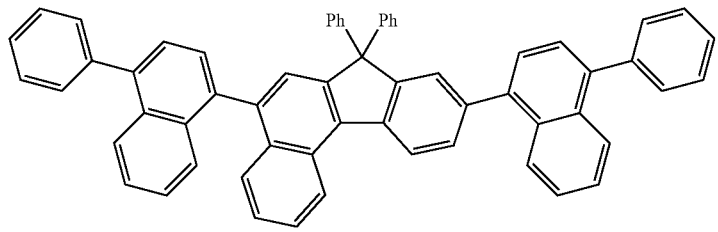
(1-17)
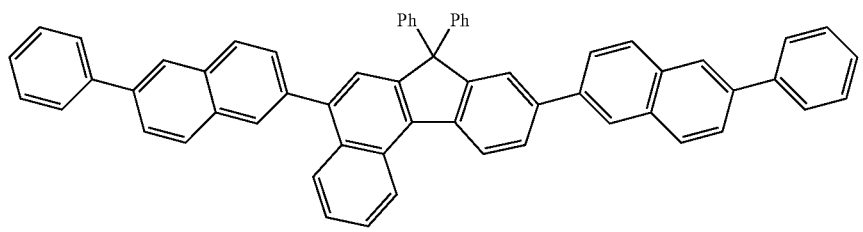
(1-18)
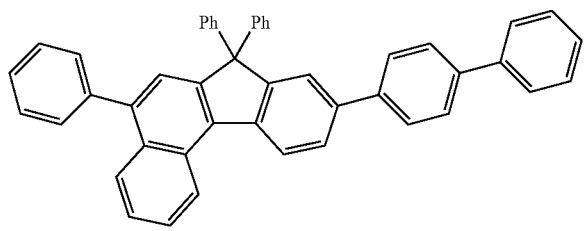
(1-19)
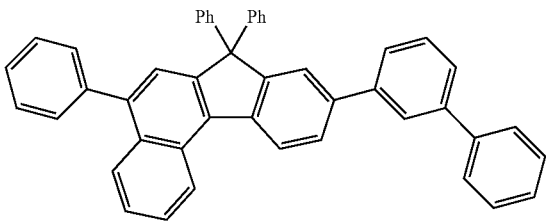
(1-20)
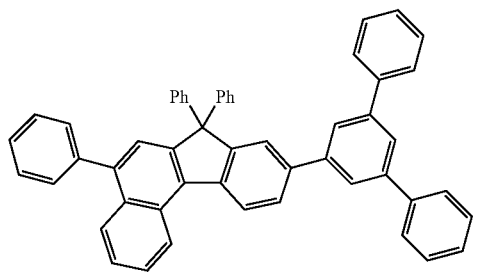
(1-21)
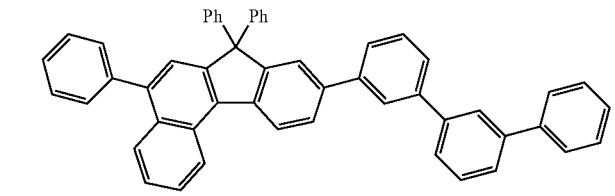
(1-22)
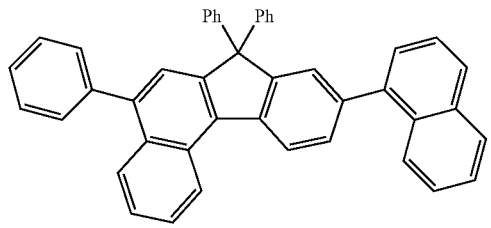
(1-23)
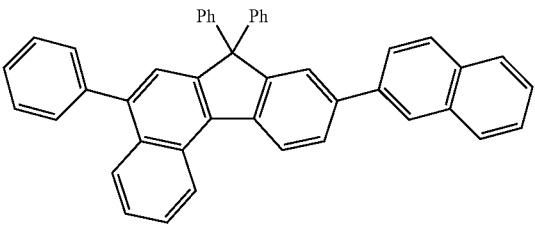
(1-24)

-continued
(1-25)
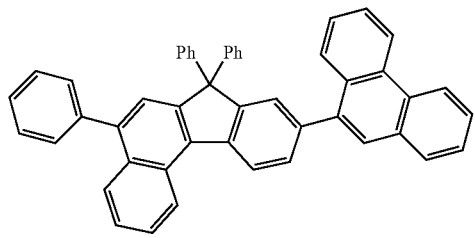
(1-26)
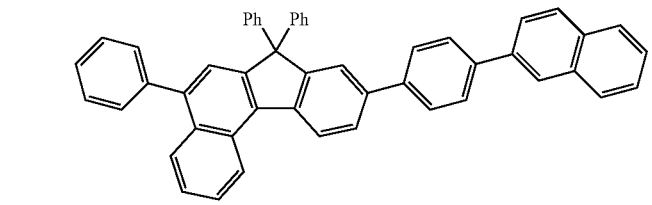
(1-27)
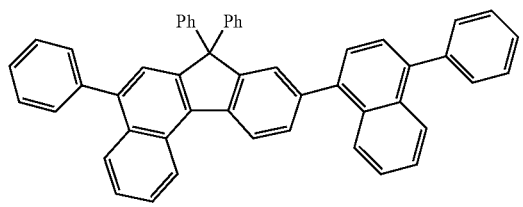
(1-28)
(1-29)
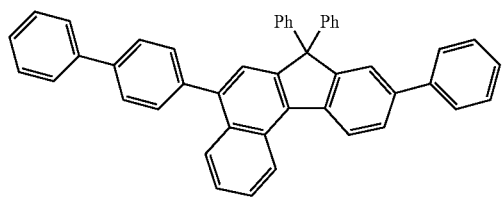
(1-30)
(1-31)
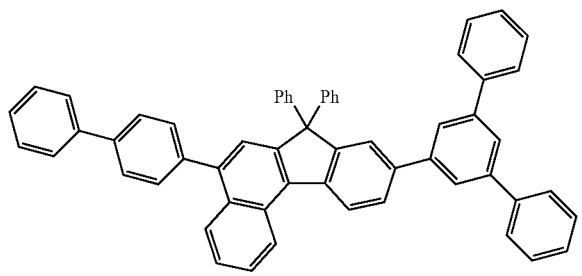
(1-32)
(1-33)
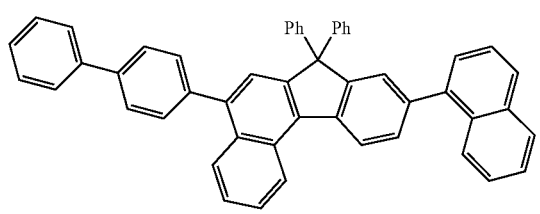
(1-34)
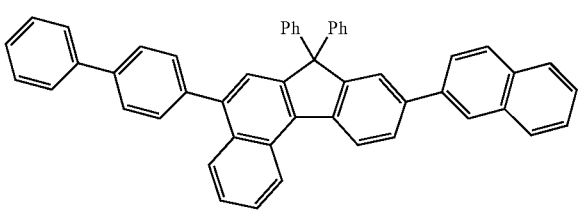
(1-35)
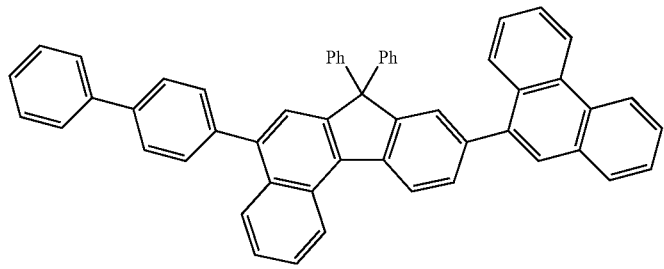

-continued
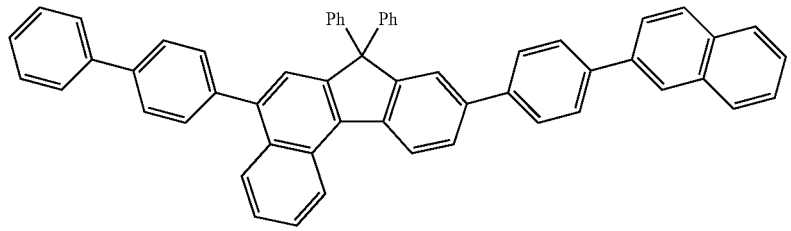
(1-36)
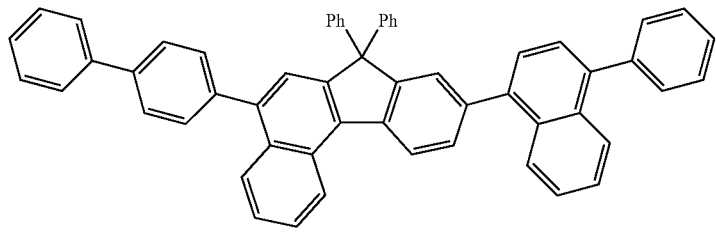
(1-37)
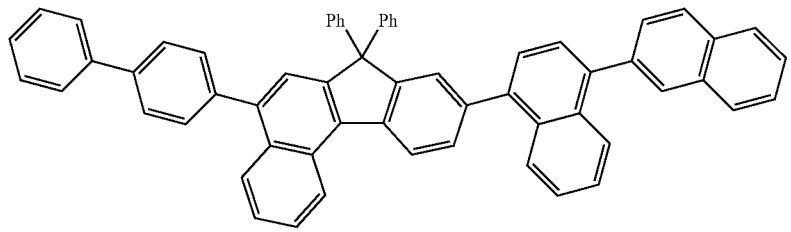
(1-38)
(1-39)
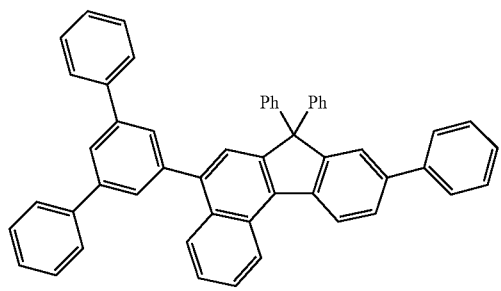
(1-40)
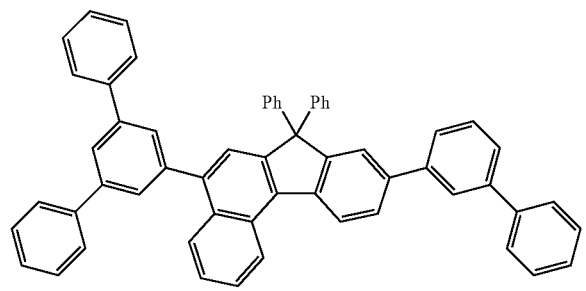
(1-41)
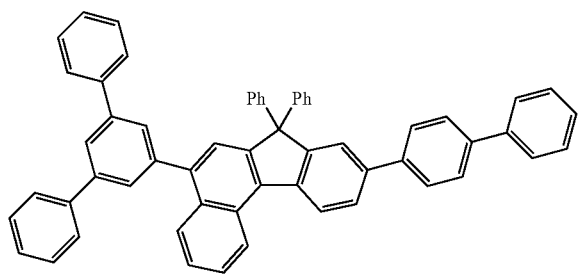
(1-42)
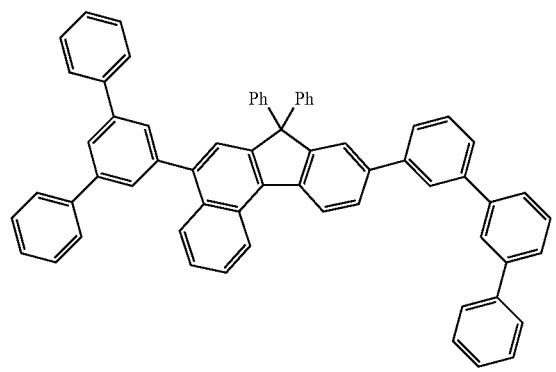

-continued
(1-43)
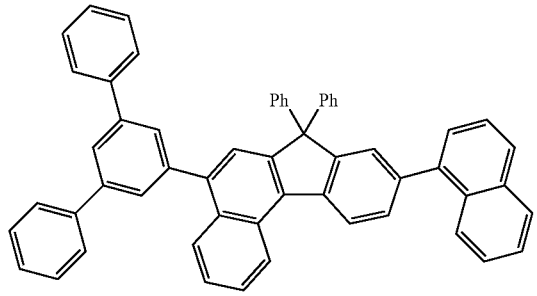
(1-44)
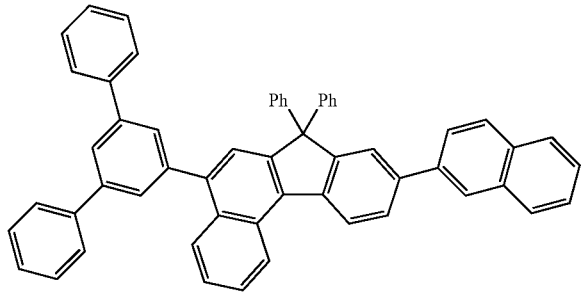
(1-45)
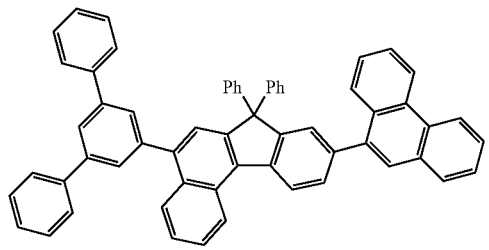
(1-46)
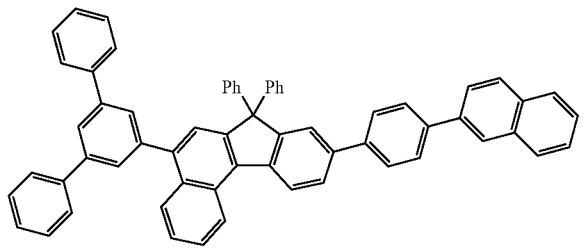
(1-47)
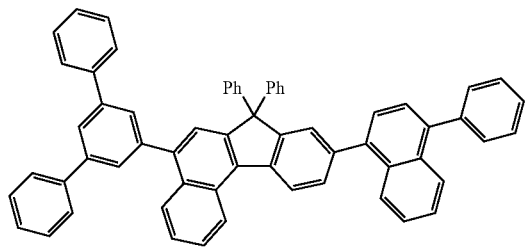
(1-48)
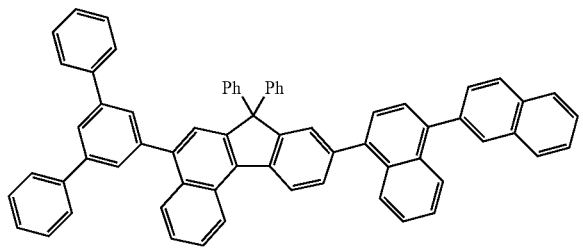
(1-49)
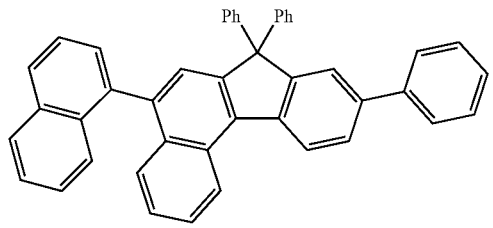
(1-50)
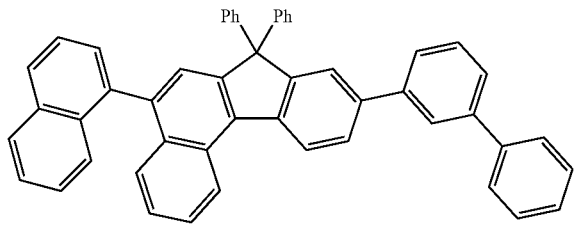
(1-51)
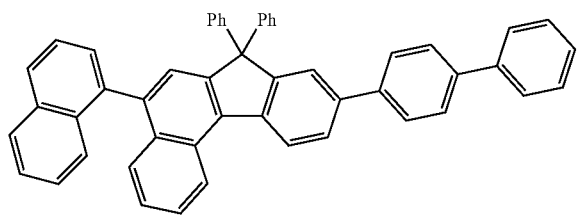
(1-52)
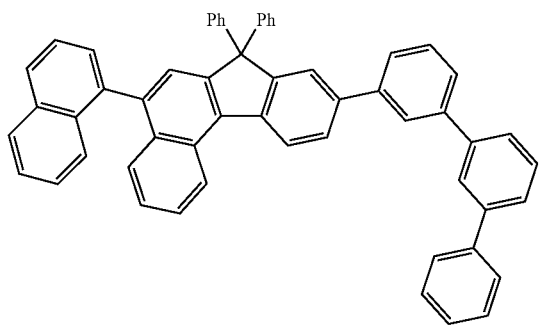

-continued
(1-53)
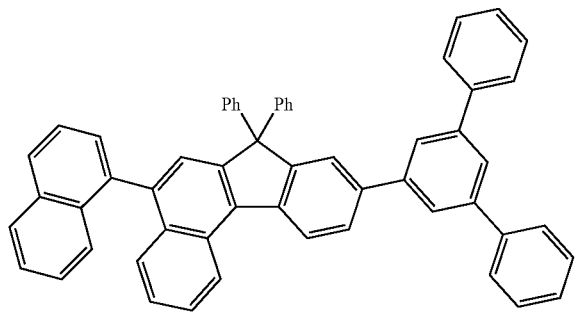
(1-54)
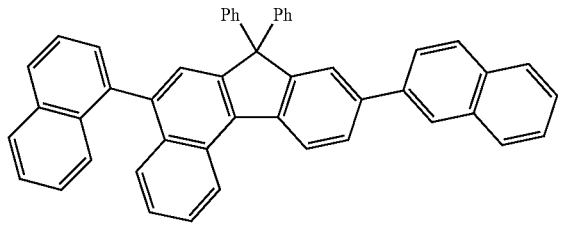
(1-55)
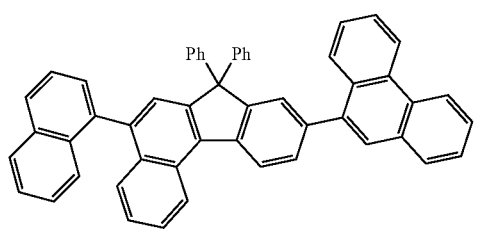
(1-56)
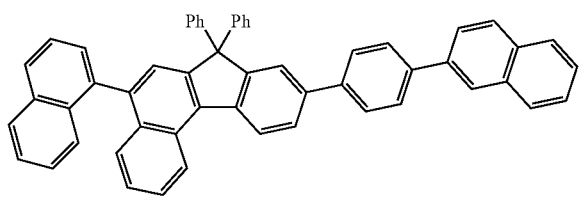
(1-57)
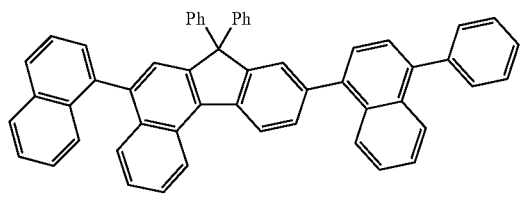
(1-58)
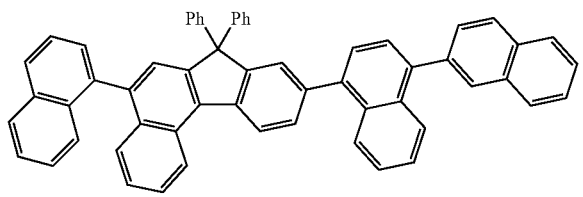
(1-59)
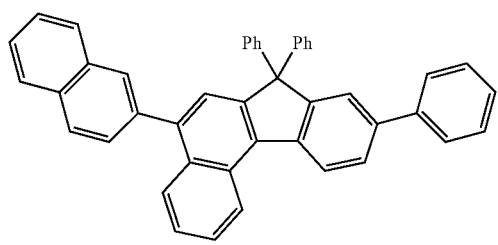
(1-60)
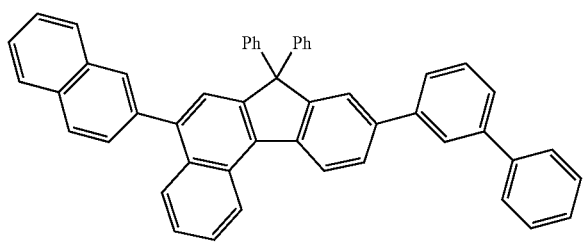
(1-61)
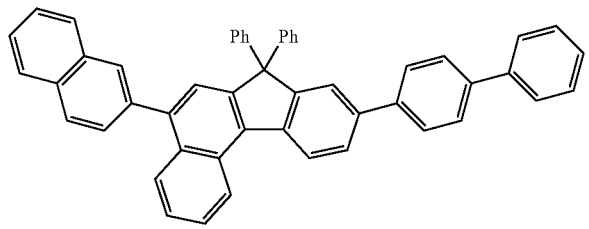
(1-62)
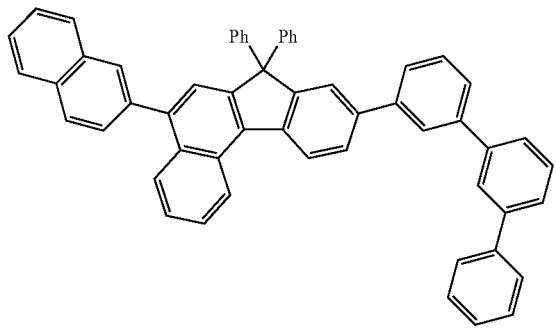

-continued
(1-63)
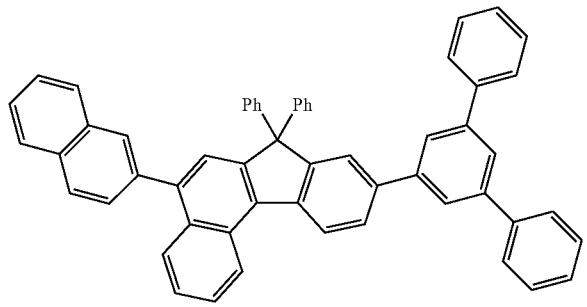
(1-64)
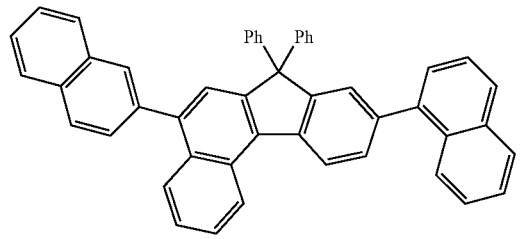
(1-65)
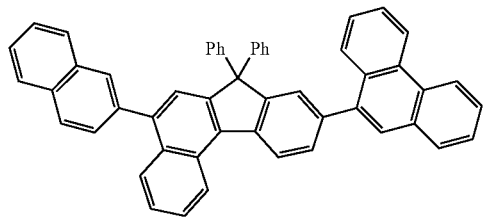
(1-66)
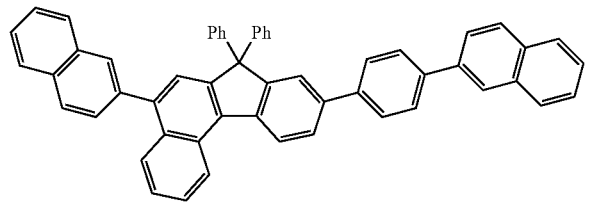
(1-67)
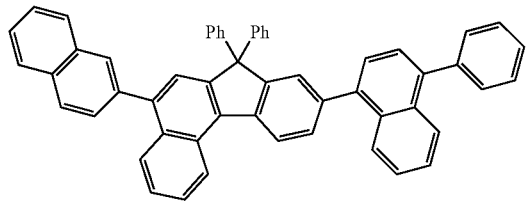
(1-68)
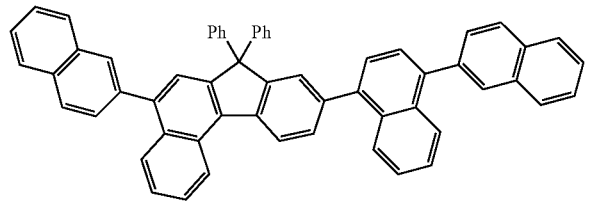
(1-69)
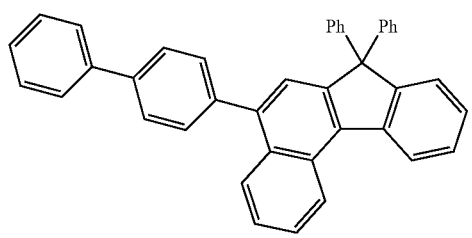
(1-70)
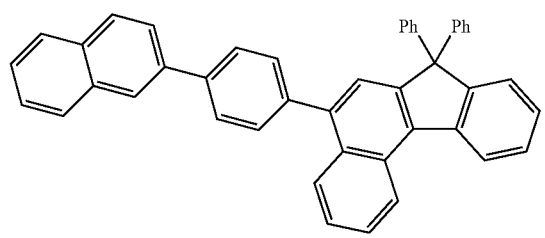
(1-71)
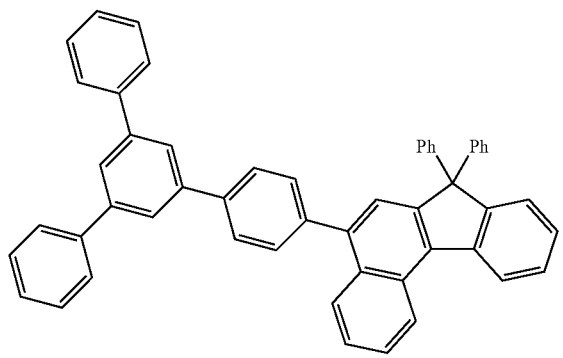
(1-72)
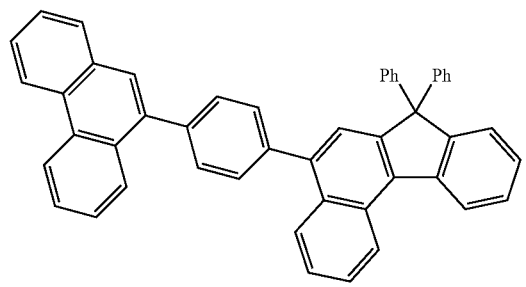

-continued
(1-73)
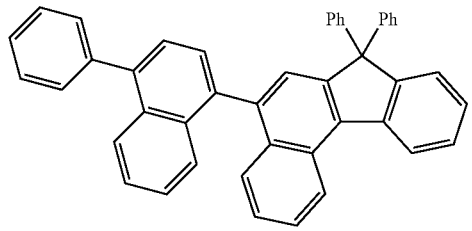
(1-74)
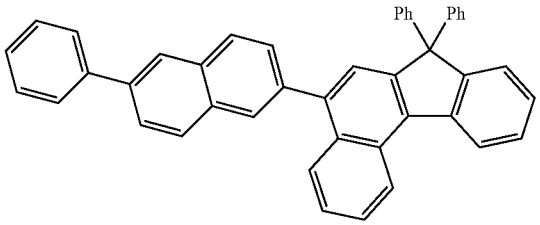
(1-75)
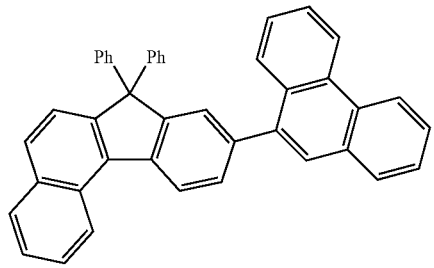
(1-76)
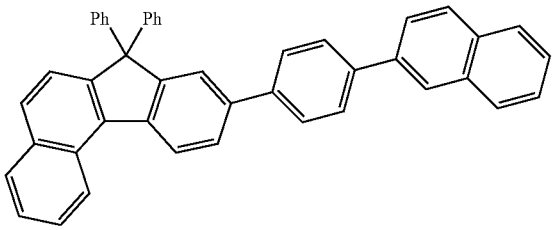
(1-77)
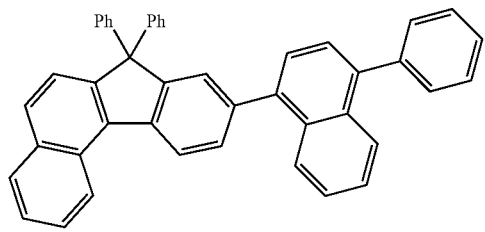
(1-78)
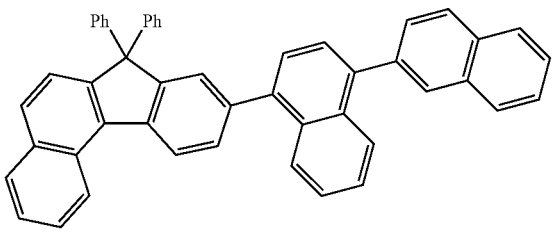
(1-79)
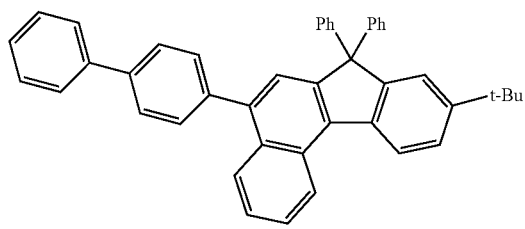
(1-80)
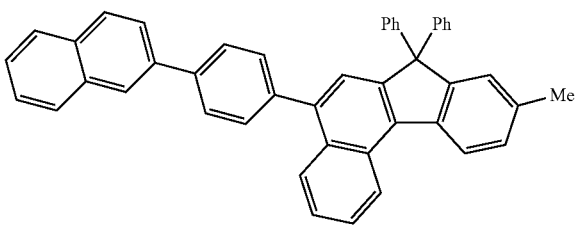
(1-81)
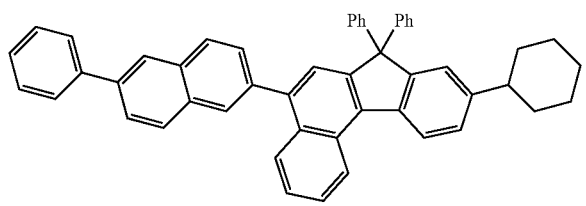
(1-82)
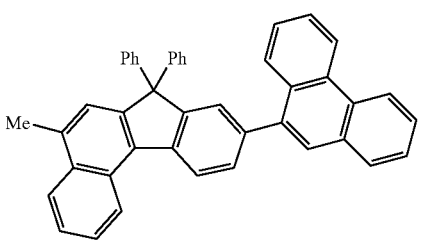
(1-83)
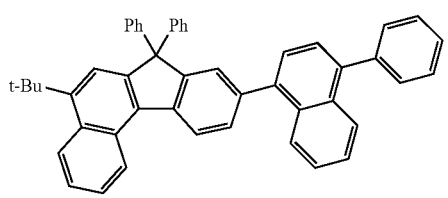
(1-84)
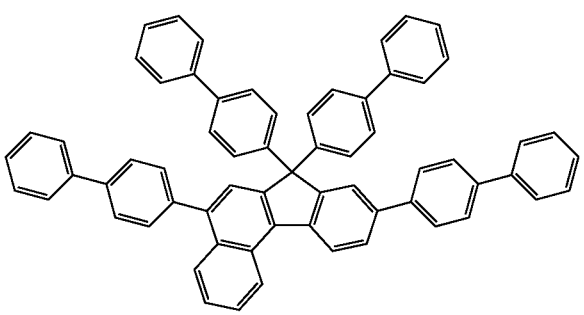

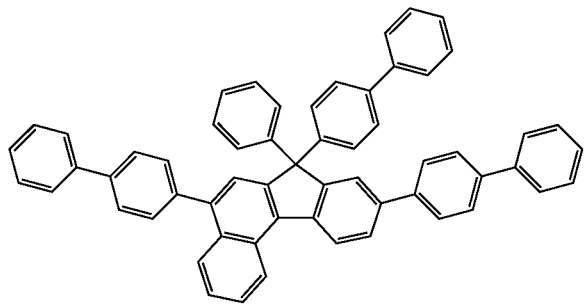

(1-85)

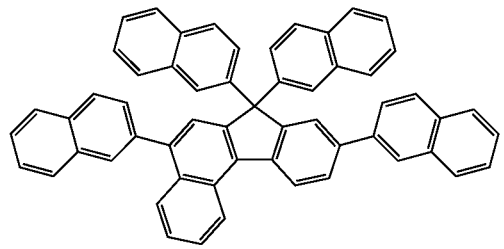

(1-86)

2. Benzofluorene Compound Represented by Formula (1')

Next, the benzofluorene compound represented by Formula (1') shall be explained.

Explanations in $Ar^1$ and $Ar^2$ of Formula (1) can be quoted for "aryl which may be substituted" in $Ar^1$ and $Ar^2$ of Formula (1'). Further, explanations in $R^1$ and $R^2$ of Formula (1) can be quoted for "alkyl which may be substituted", "cycloalkyl which may be substituted" and "aryl which may be substituted" in $R^2$ of Formula (1').

"Diarylamino having aryl which may be substituted" in $R^1$ and $R^2$ of Formula (1') is amino substituted with two "aryls which may be substituted". The "aryls which may be substituted" may be the same or different, and they are preferably the same. "Aryl" of "aryl which may be substituted" includes, for example, aryl having 6 to 30 carbon atoms, and it includes preferably aryl having 6 to 24 carbon atoms, more preferably aryl having 6 to 20 carbon atoms, further preferably aryl having 6 to 16 carbon atoms and particularly preferably aryl having 6 to 12 carbon atoms.

To be specific, "aryl" of "aryl which may be substituted" includes, for example, the "aryls" described above, and more preferred "aryl" is phenyl, biphenylyl, naphthyl and the like, and the particularly preferred "aryl" is phenyl.

The "substituents" for "aryl which may be substituted" are alkyl, aryl, heteroaryl or the like, and the preferred examples of the alkyl and the aryl include the "alkyls" and the "aryls" each described above. Further, the preferred examples of heteroaryl include the following groups.

The "heteroaryl" includes, for example, heteroaryl having 2 to 30 carbon atoms. The preferred "heteroaryl" is heteroaryl having 2 to 25 carbon atoms, and it is more preferably heteroaryl having 2 to 20 carbon atoms, further preferably heteroaryl having 2 to 15 carbon atoms and particularly preferably heteroaryl having 2 to 10 carbon atoms.

Further, the "heteroaryl" includes, for example, heterocyclic groups containing 1 to 5 hetero atoms selected from oxygen atoms, sulfur atoms and nitrogen atoms other than carbon atoms as ring constitutional atoms, and it includes, for example, aromatic heterocyclic groups.

The "heterocyclic group" includes, for example, pyrrolyl, oxazolyl, isooxazolyl, thiazolyl, isothiazolyl, imidazolyl, oxadiazolyl, thiadiazolyl, triazolyl, tetrazolyl, pyrazolyl, pyridyl, pyrimidinyl, pyridazinyl, pyrazinyl, triazinyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathienyl, thianthrenyl, indolidinyl and the like, and imidazolyl, pyridyl, carbazolyl and the like are preferred.

The "aromatic heterocyclic group" includes, for example, furyl, thienyl, pyrrolyl, oxazolyl, isooxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathienyl, thianthrenyl, indolidinyl and the like, and thienyl, imidazolyl, pyridyl, carbazolyl and the like are preferred.

The specific examples of the compound represented by Formula (1') described above include, for example, compounds represented by the following Formulas (1'-1) to (1'-16). Among the compounds shown below, particularly preferred are the compounds represented by the following Formula (1'-1), Formula (1'-2), Formula (1'-6), Formula (1'-9) and Formula (1'-15).

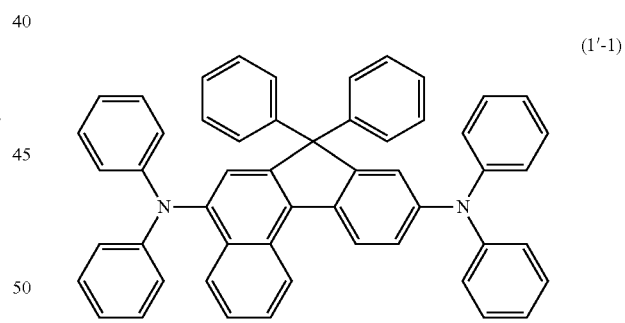

(1'-1)

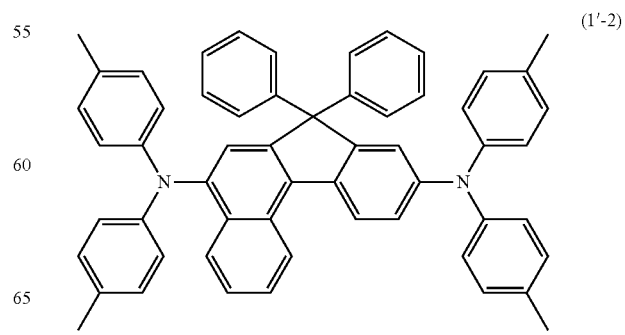

(1'-2)

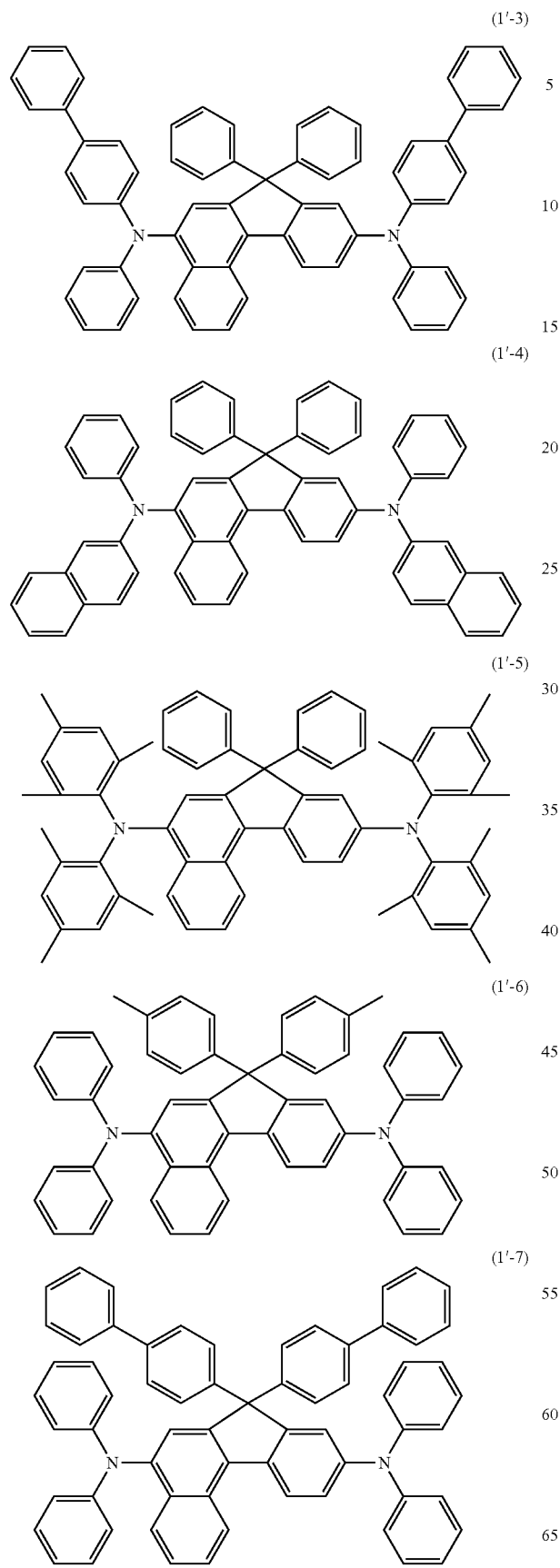
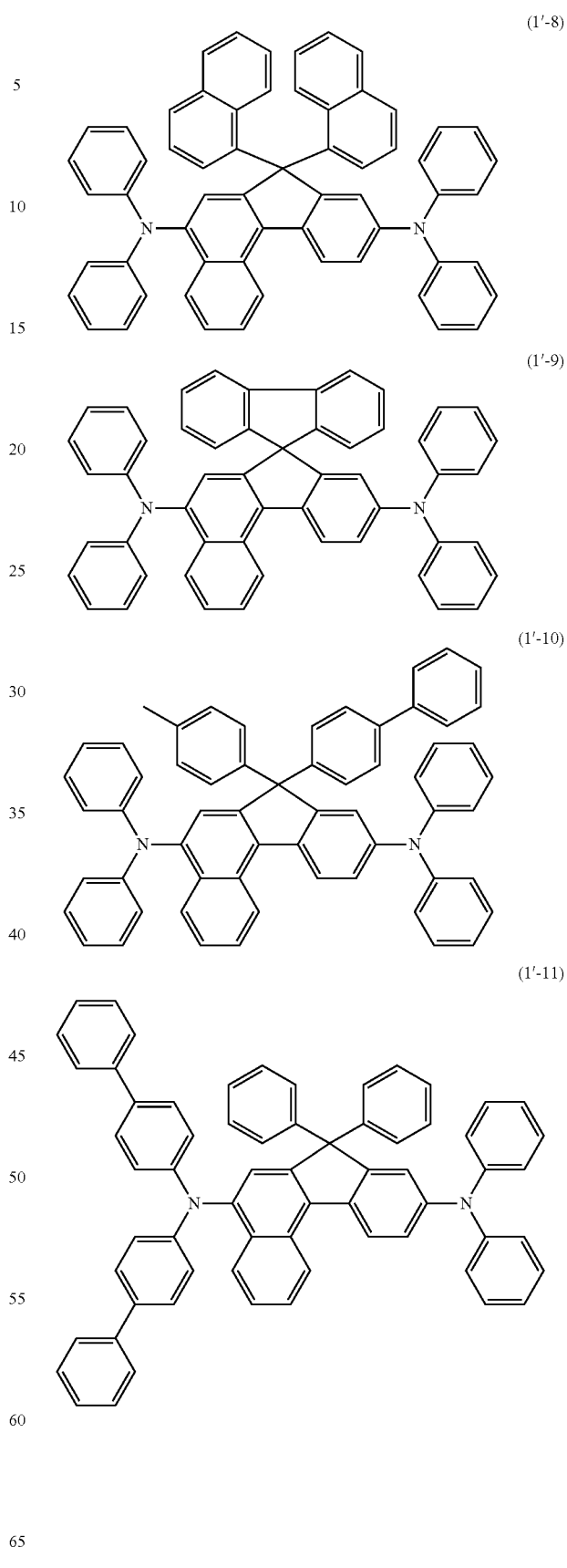

(1'-12)

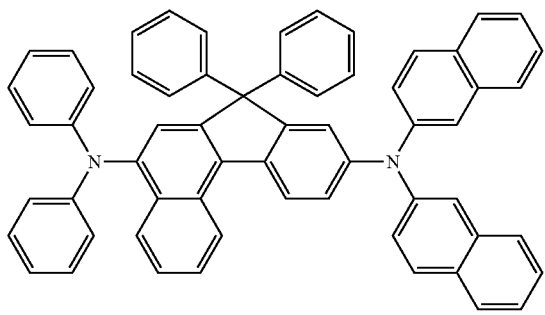

(1'-13)

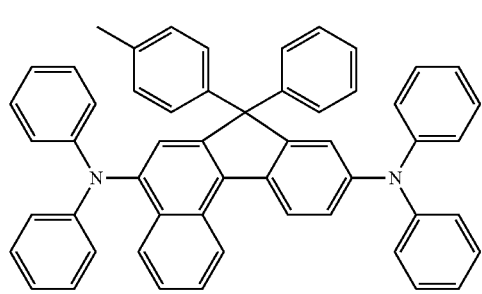

(1'-14)

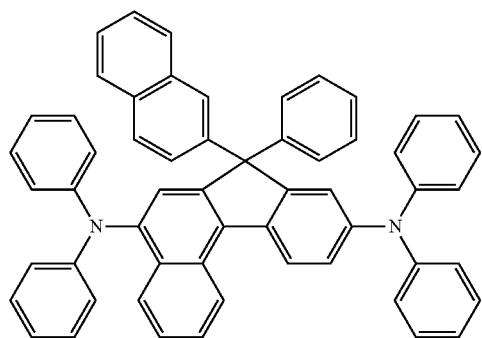

(1'-15)

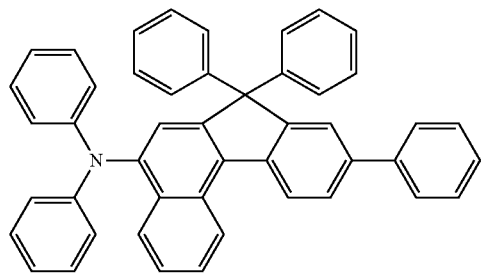

(1'-16)

for example, a Suzuki coupling reaction. The Suzuki coupling reaction is reaction in which aromatic halide or triflate is subjected to coupling with aromatic boronic acid or aromatic boronic ester under the presence of a base using a palladium catalyst. A specific example of a reaction route for obtaining the compound represented by Formula (1) by the reaction is shown below (schemes 1 to 3). $Ar^1$, $Ar^2$, $R^1$ and $R^2$ in the respective schemes are the same as described above, and TfO is triflate.

(Scheme 1)

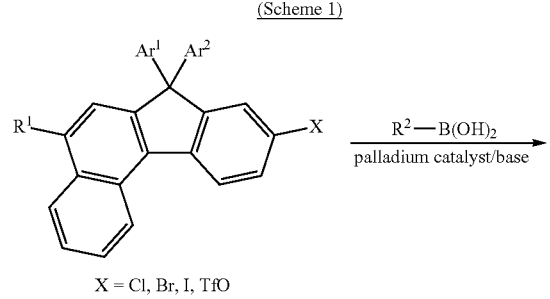

Formula (1)

(Scheme 2)

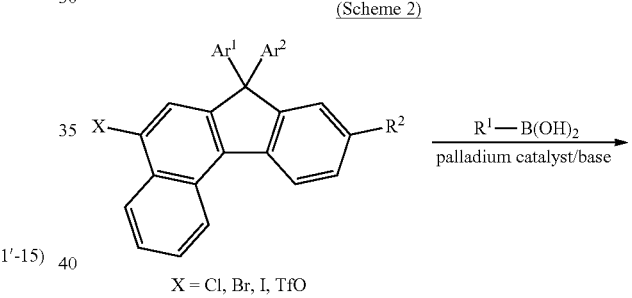

Formula (1)

(Scheme 3)

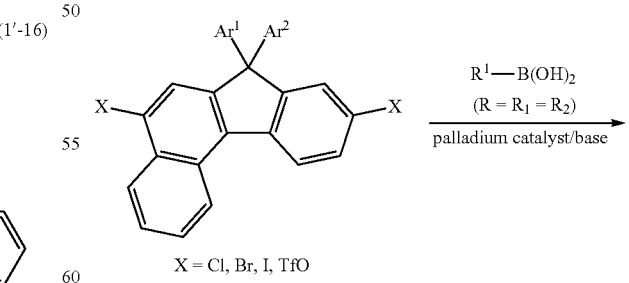

Formula (1)

3. Production Process for Benzofluorene Compound
<Benzofluorene Compound Represented by Formula (1)>
The benzofluorene compound represented by Formula (1) can be produced by using a known synthetic method such as, The specific examples of the palladium catalyst used in the reaction are $Pd(PPh_3)_4$, $PdCl_2(PPh_3)_2$, $Pd(OAc)_2$, tris(dibenzylideneacetone)dipalladium (0), tris(dibenzylideneacetone)

dipalladium (0) chloroform complex, bis(dibenzylideneacetone)palladium (0) and the like. A phosphine compound may be added, if necessary, to the palladium compounds in order to accelerate the reaction. The specific examples of the phosphine compound include tri(t-butyl)phosphine, tricyclohexylphosphine, 1-(N,N-dimethylaminomethyl)-2-(di-t-butylphosphino)ferrocene, 1-(N,N-dibutylaminomethyl)-2-(di-t-butylphosphino)ferrocene, 1-(methoxymethyl)-2-(di-t-butylphosphino)ferrocene, 1,1'-bis(di-t-butylphosphino)ferrocene, 2,2'-bis(di-t-butylphosphino)-1,1'-binaphthyl, 2-methoxy-2'-(di-t-butylphosphino)-1,1'-binaphthyl and the like.

The specific examples of the base used in the reaction are sodium carbonate, potassium carbonate, cesium carbonate, sodium hydrogencarbonate, sodium hydroxide, potassium hydroxide, barium hydroxide, sodium ethoxide, sodium t-butoxide, sodium acetate, tripotassium phosphate, potassium fluoride and the like.

Further, the specific examples of the solvent used in the reaction are benzene, toluene, xylene, N,N-dimethylformamide, tetrahydrofuran, diethyl ether, t-butyl methyl ether, 1,4-dioxane, methanol, ethanol, isopropyl alcohol and the like. These solvents can suitably be selected according to the structures of aromatic halide, triflate, aromatic boronic ester and aromatic boronic acid which is subjected to the reaction. The solvent may be used alone or in the form of a mixed solvent.

<Benzofluorene Compound Represented by Formula (1')>

When $R^1$ and $R^2$ are diarylamino having aryl which may be substituted in Formula (1'), the benzofluorene compound represented by Formula (1') can be produced by using an existing reaction such as a Buchwald-Hartwig reaction or a Ullmann reaction. The Buchwald-Hartwig reaction is reaction in which aromatic halide is subjected to coupling with primary aromatic amine or secondary aromatic amine under the presence of a base using a palladium catalyst or a copper catalyst. A specific example of a reaction route for obtaining the compound represented by Formula (1') by the reaction is shown below (schemes 4 to 7).

$Ar^1$ and $Ar^2$ in the respective schemes are the same as described above, and $R^1$ and $R^2$ are diarylamino having aryl which may be substituted. $R^3$ and $R^4$ are "aryl which may be substituted" constituting "diarylamino having aryl which may be substituted".

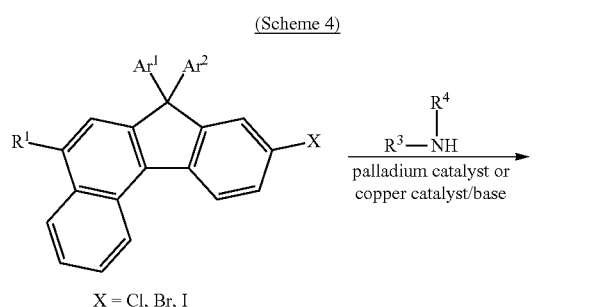

(Scheme 4)

X = Cl, Br, I

Formula (1')

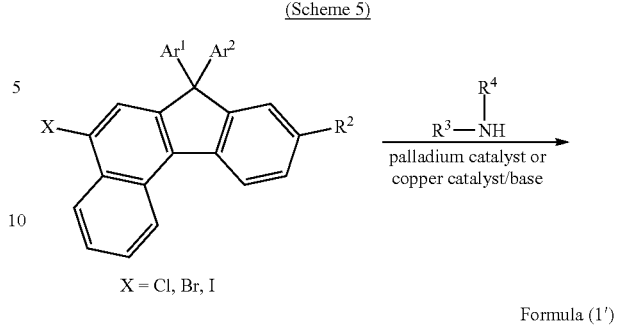

(Scheme 5)

X = Cl, Br, I

Formula (1')

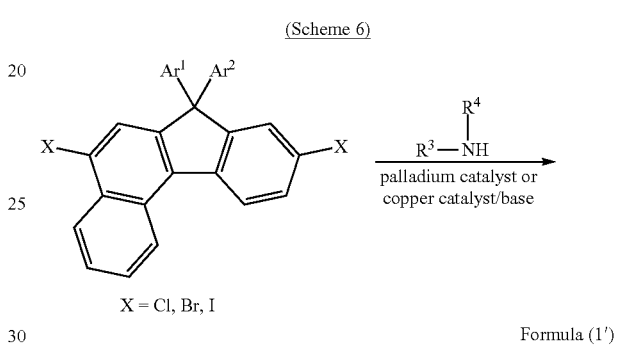

(Scheme 6)

X = Cl, Br, I

Formula (1')

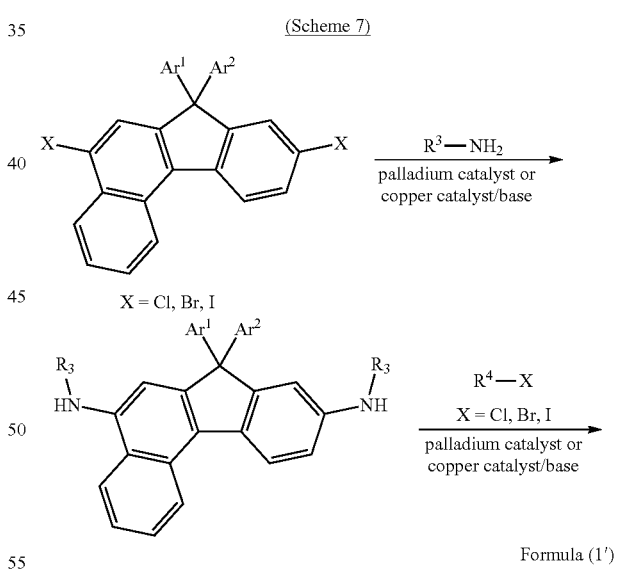

(Scheme 7)

X = Cl, Br, I

Formula (1')

The specific examples of the palladium catalyst, the base and the solvent which are used in the reaction can be selected from those used in the Suzuki coupling reaction. A phosphine compound may be added, if necessary, to the palladium compounds in order to accelerate the reaction. The specific examples of the phosphine compound can be selected as well from the same compounds as the specific examples shown in the Suzuki coupling reaction. In addition to the compounds, 1,1'-bis(diphenylphosphino)ferrocene, bis(diphenylphosphino)binaphthyl and the like can be used as well.

The Ullmann reaction is reaction in which aromatic halide is subjected to coupling with primary aromatic amine or secondary aromatic amine under the presence of a base using a copper catalyst. The specific examples of the copper catalyst used in the reaction are copper powder, copper chloride, copper bromide, copper iodide and the like. The specific examples of the base used in the reaction can be selected from the same compounds as in the Suzuki coupling reaction. The specific examples of the solvent used in the reaction are nitrobenzene, dichlorobenzene, N,N-dimethylformamide and the like.

Also, in a case where $R^1$ is diarylamino having aryl which may be substituted and where $R^2$ is hydrogen, alkyl which may be substituted, cycloalkyl which may be substituted or aryl which may be substituted in Formula (1'), the compound represented by Formula (1') can be produced by the scheme 5.

In the case, $R^2$ in the scheme 5 is hydrogen, alkyl which may be substituted, cycloalkyl which may be substituted or aryl which may be substituted. $Ar^1$ and $Ar^2$ in the scheme 5 are the same as described above, and $R^3$ and $R^4$ are "aryl which may be substituted" constituting "diarylamino having aryl which may be substituted".

The benzofluorene compounds represented by Formula (1) and Formula (1') are compounds having strong fluorescence in a solid state and can be used for emission of various colors, and they are suited particularly to emission of a blue color. Among the benzofluorene compounds represented by Formula (1) and Formula (1'), the compounds having an asymmetric molecular structure are liable to form an amorphous state in producing an organic EL device. Further, they are excellent in heat resistance and stable in applying an electric field.

The benzofluorene compound represented by Formula (1) is effective as a host emission material. The benzofluorene compound has a shorter emission wavelength, and it is excellent particularly as a blue host emission material but can be used as well for emission of colors other than a blue color. When the benzofluorene compound is used as a host material, energy transfer is efficiently carried out, and a light emitting device having high efficiency and long life can be obtained.

Further, the benzofluorene compound represented by Formula (1') is effective particularly as a dopant material.

The benzofluorene compounds represented by Formula (1) and Formula (1') comprise benzo[c]fluorene in a fluorene skeleton and therefore are excellent in solubility in solvents as compared with compounds having a benzo[a]fluorene skeleton. Accordingly, width in selecting a solvent in synthesis is broad, and therefore freedom of the synthesis can be enhanced, and mass production can be easy. Further a spin coating method using various solvents can readily be employed.

The benzofluorene compound represented by Formula (1') is substituted with diaryl amino in a $R^1$ position without fail. This compound has high heat resistance as compared with the compound substituted with diaryl amino only in a $R^2$ position, and it is improved in luminous efficiency when applied to a device.

4. Organic Electroluminescent Device

The benzofluorene compound according to the present invention can be used, for example, as a material for an organic electroluminescent device.

The organic electroluminescent device according to this embodiment shall be explained in details with reference to a drawing. FIG. 1 is an outline cross-sectional drawing showing the organic electroluminescent device according to the present embodiment.

<Structure of Organic Electroluminescent Device>

An organic electroluminescent device 100 shown in FIG. 1 comprises a substrate 101, an anode 102 provided on the substrate 101, a hole injection layer 103 provided on the anode 102, a hole transport layer 104 provided on the hole injection layer 103, an emission layer 105 provided on the hole transport layer 104, an electron transport layer 106 provided on the emission layer 105, an electron injection layer 107 provided on the electron transport layer 106 and a cathode 108 provided on the electron injection layer 107.

The organic electroluminescent device 100 may be turned upside down in a preparation order and may assume a structure in which it comprises, for example, the substrate 101, the cathode 108 provided on the substrate 101, the electron injection layer 107 provided on the cathode 108, the electron transport layer 106 provided on the electron injection layer 107, the emission layer 105 provided on the electron transport layer 106, the hole transport layer 104 provided on the emission layer 105, the hole injection layer 103 provided on the hole transport layer 104 and the anode 102 provided on the hole injection layer 103.

All the respective layers described above do not necessarily have to be present, and the hole injection layer 103, the hole transport layer 104, the electron transport layer 106 and the electron injection layer 107 are layers which are optionally provided, wherein a minimum structural unit assumes a structure comprising the anode 102, the emission layer 105 and cathode 108. The respective layers described above each may comprise a single layer or plural layers.

The mode of the layers constituting the organic electroluminescent device may be, in addition to the structural mode of "substrate/anode/hole injection layer/hole transport layer/emission layer/electron transport layer/electron injection layer/cathode" described above, the structural modes of "substrate/anode/hole transport layer/emission layer/electron transport layer/electron injection layer/cathode", "substrate/anode/hole injection layer/emission layer/electron transport layer/electron injection layer/cathode" "substrate/anode/hole injection layer/hole transport layer/emission layer/electron injection layer/cathode", "substrate/anode/hole injection layer/hole transport layer/emission layer/electron transport layer/cathode", "substrate/anode/emission layer/electron transport layer/electron injection layer/cathode", "substrate/anode/hole transport layer/emission layer/electron injection layer/cathode", "substrate/anode/hole transport layer/emission layer/electron transport layer/cathode", "substrate/anode/hole injection layer/emission layer/electron injection layer/cathode", "substrate/anode/hole injection layer/emission layer/electron transport layer/cathode", "substrate/anode/hole injection layer/hole transport layer/emission layer/cathode", "substrate/anode/hole injection layer/emission layer/cathode", "substrate/anode/hole transport layer/emission layer/cathode", "substrate/anode/emission layer/electron transport layer/cathode", "substrate/anode/emission layer/electron injection layer/cathode" and "substrate/anode/emission layer/cathode".

<Substrate in the Organic Electroluminescent Device>

The substrate 101 is a base for the organic electroluminescent device 100, and quartz, glass, metal, plastics and the like are usually used therefor. The substrate 101 is formed in the shape of a plate, a film or a sheet according to the purposes, and a glass plate, a metal plate, a metal foil, a plastic film or a plastic sheet is used therefor. Among them, a glass plate and a plate made of a transparent synthetic resin such as polyester, polymethacrylate, polycarbonate and polysulfone are preferred. Soda lime glass, non-alkali glass and the like are used for the glass substrate. The thickness thereof may be such a thickness as enough for maintaining the mechanical strength, and therefore it is, for example, 0.2 mm or more. An upper limit value of the thickness is, for example, 2 mm or less, preferably 1 mm or less. The material of glass is preferably non-alkali glass since ions eluted from glass are preferably fewer. Soda lime glass which is provided with a barrier coat such as $SiO_2$ is commercially available, and therefore it can be used. The substrate 101 may be provided at least on one face thereof with a gas barrier film such as a minute silicon oxide film in order to enhance gas barrier property thereof. Particularly when a plate, a film or a sheet made of a synthetic resin having low gas barrier property is used for the substrate 101, a gas barrier membrane is preferably provided thereon.

<Anode in the Organic Electroluminescent Device>

The anode 102 plays a role of injecting holes into the emission layer 105. When the hole injection layer 103 and/or the hole transport layer 104 are provided between the anode 102 and the emission layer 105, holes are injected into the emission layer 105 via these layers.

A material for forming the anode 102 includes inorganic compounds and organic compounds. The inorganic compounds include, for example, metals (aluminum, gold, silver, nickel, palladium, chromium and the like), metal oxides (oxide of indium, oxide of tin, indium-tin oxide (ITO) and the like), halogenated metals (copper iodide and the like), copper sulfide, carbon black, ITO glass, nesa glass and the like. The organic compounds include, for example, polythiophene such as poly(3-methylthiophene) and electrically conductive polymers such as polypyrrole, polyaniline and the like. In addition thereto, those suitably selected from materials used for an anode of an organic electroluminescent device can be used.

A resistance of the transparent electrode shall not be restricted as long as an electric current sufficient for emission of the light emitting device can be supplied, and it is preferably a low resistance from the viewpoint of power consumption of the light emitting device. For example, an ITO substrate having a resistance of 300 Ω/square or less functions as a device electrode. At present, a substrate having a resistance of about 10 Ω/square can be supplied, and therefore a product having a low resistance of, for example, 100 to 5 Ω/square, preferably 50 to 5 Ω/square is particularly preferably used. A thickness of ITO can optionally be selected depending on a resistance value thereof, and it is usually used in a range of 100 to 300 nm in many cases.

<Hole Injection Layer and Hole Transport Layer in the Organic Electroluminescent Device>

The hole injection layer 103 plays a role of efficiently injecting holes moving from the anode 102 into the emission layer 105 or the hole transport layer 104. The hole transport layer 104 plays a role of efficiently transporting holes injected from the anode 102 or holes injected from the anode 102 via the hole injection layer 103 to the emission layer 105. The hole injection layer 103 and the hole transport layer 104 are formed respectively by laminating or mixing one or more hole injecting or transporting material(s) or from a mixture of the hole injecting or transporting material(s) with a high molecular binder. Further, inorganic salt such as iron chloride (III) may be added to the hole injecting or transporting material to form the layers.

The hole injecting or transporting material has to efficiently inject or transport holes from a positive electrode between the electrodes to which an electrical field is applied, and it is desirable that the hole injection efficiency is high and that the holes injected are efficiently transported. Accordingly, preferred is the material which has small ionization potential and large hole mobility and is excellent in stability and in which impurities trapped are less liable to be generated in producing and using.

Optional compounds selected from compounds which have so far conventionally been used as a charge transport material for a hole in a photoconductive material, p type semiconductors and publicly known compounds used for a hole injection layer and a hole transport layer in an organic electroluminescent device can be used as materials for forming the hole injection layer 103 and the hole transport layer 104. The specific examples thereof are preferably carbazole derivatives (N-phenylcarbazole, polyvinylcarbazole and the like), biscarbazole derivatives such as bis(N-alkylcarbazole) and bis(N-alkylcarbazole), triarylamine derivatives (polymers having aromatic tertiary amine on a main chain or a side chain), triphenylamine derivatives such as 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl (hereinafter abbreviated as NPD), N,N'-diphenyl-N,N'-di(3-methylphenyl)-4,4'-diphenyl-1,1'-diamine, N,N'-dinaphthyl-N,N'-diphenyl-4,4'-diphenyl-1,1'-diamine and 4,4',4"-tris(3-methylphenyl(phenyl)-amino)triphenylamine, starburst amine derivatives and the like, stilbene derivatives, heterocyclic compounds such as phthalocyanine derivatives (non-metal phthalocyanines, copper phthalocyanine and the like), pyrazoline derivatives, hydrazone compounds, benzofuran derivatives, thiophene derivatives, oxadiazole derivatives and porphylin derivatives, polysilane and the like. In polymer compounds, polycarbonate, styrene derivatives, polyvinylvcarbazole, polysilane and the like which have the monomers described above on side chains are preferred, but they shall not specifically be restricted as long as they are compounds which can form a thin film necessary for preparing a light emitting device and which can inject holes from an anode and can transport the holes.

It is know as well that electrical conductivity of an organic semiconductor is strongly influenced by doping thereof. Such organic semiconductor matrix substance is constituted from a compound having good electron donating property or a compound having good electron accepting property. Strong electron acceptors such as tetracyanoquinonedimethane (TCNQ) or 2,3,5,6-tetrafluorotetracyano-1,4-benzoquinonedimethane (F4TCNQ) are known for doping electron donating substances (refer to, for example, a document "M. Pfeiffer, A. Beyer, T. Fritz, K. Leo, Appl. Phys. Lett., 73 (22), 3202 to 3204 (1998)" and a document "J. Blochwitz, M. Pfeiffer, T. Fritz, K. Leo, Appl. Phys. Lett., 73 (6), 729 to 731 (1998)"). They produce so-called holes by an electron moving process in an electron donating type base material (hole transport material). Conductivity of the base material is changed to a considerably large extent by the number and mobility of holes. Known as a matrix substance having hole transport property are, for example, benzidine derivatives (TPD and the like), starburst amine derivatives (TDATA and the like) and specific metal phthalocyanines (particularly zinc phthalocyanine ZnPc and the like) (JP H17-167175 A/2005).

<Emission Layer in the Organic Electroluminescent Device>

The emission layer 105 emits light by recombining holes injected from the anode 102 with electrons injected from the cathode 108 between the electrodes to which an electrical field is applied. A material for forming the emission layer 105 may be any compounds as long as they are compounds (luminescent compounds) which are excited by recombination of holes with electrons to emit light, and they are preferably compounds which can form a stable thin film shape and which show strong emission (luminescence and/or phosphorescence) efficiency in a solid state.

The emission layer may comprise either a single layer or plural layers and is formed by an emission material (host material and dopant material). This may be either a mixture of a host material and a dopant material or a host material alone. That is, only the host material or the dopant material may emit light or both the host material and the dopant material may emit light in the respective layers of the emission layer. The host material and the dopant material each may comprise either one kind or combination of two or more kinds thereof. The dopant material may be contained in either the whole part or a part of the host material. A use amount of the dopant is varied depending on the dopant and can be determined so that the use amount meets the characteristics of the dopant (for example, a too large use amount of the dopant is likely to bring about a concentration quenching phenomenon). A standard of a use amount of the dopant is preferably 0.001 to 50% by weight, more preferably 0.1 to 10% by weight and further preferably 1 to 5% by weight based on the whole emission material. In a doping method, the emission layer can be formed by a method of co-depositing with the host material, or the dopant material may be mixed in advance with the host material and then deposited at the same time.

Further, the emission material for the light emitting device according to the present embodiment may be either fluorescent or phosphorescent.

The benzofluorene compound represented by Formula (1) described above can be used as the host material. In particular, preferably used are the compounds represented by the foregoing Formula (1-1), Formula (1-3), Formula (1-4), Formula (1-7), Formula (1-12), Formula (1-13), Formula (1-14), Formula (1-19), Formula (1-23), Formula (1-24), Formula (1-29), Formula (1-31), Formula (1-33), Formula (1-34), Formula (1-41), Formula (1-43), Formula (1-44), Formula (1-49), Formula (1-51), Formula (1-53), Formula (1-54), Formula (1-59), Formula (1-61), Formula (1-63), Formula (1-64), Formula (1-65), Formula (1-84) and Formula (1-86). Further, more preferably used are the compounds represented by the foregoing Formula (1-1), Formula (1-4), Formula (1-7), Formula (1-12), Formula (1-13), Formula (1-14), Formula (1-24), Formula (1-29), Formula (1-31), Formula (1-34), Formula (1-44), Formula (1-59), Formula (1-61), Formula (1-63) and Formula (1-65). A use amount of the benzofluorene compound represented by the foregoing Formula (1) as the host material is preferably 50 to 99.999% by weight, more preferably 80 to 99.95% by weight and further preferably 90 to 99.9 by weight based on the whole emission material.

Other host materials shall not specifically be restricted, and suitably used are condensed ring derivatives such as anthracene, pyrene and the like which have so far been known as an emission material, metal chelated oxynoid compounds including tris(8-quinolinolate)aluminum, bisstyryl derivatives such as bisstyrylanthracene derivatives, distyrylbenzene derivatives and the like, tetraphenylbutadiene derivatives, coumarin derivatives, oxadiazole derivatives, pyrrolopyridine derivatives, perinone derivatives, cyclopentadiene derivatives, oxadiazole derivatives, thiadiazolopyridine derivatives, pyrrolopyrrole derivatives and polymers such as polyphenylenevinylene derivatives, polyparaphenylene derivatives and polythiophene derivatives.

In addition to the compounds, compounds suitably selected from compounds described in Kagaku Kogyo (Chemical Industry) issued in June 2004 edition, p. 13 and references cited therein can be used as the host material.

The benzofluorene compound represented by Formula (1') described above can be used as the dopant material, and in particular, more preferably used are the compounds represented by the foregoing Formula (1'-1), Formula (1'-2), Formula (1'-6), Formula (1'-9) and Formula (1'-15). A use amount of the benzofluorene compound represented by the foregoing Formula (1') as the dopant material is preferably 0.001 to 50% by weight, more preferably 0.05 to 20% by weight and further preferably 0.1 to 10% by weight based on the whole emission material. In a doping method, the emission layer can be formed by a method of co-depositing with the host material, or the dopant material may be mixed in advance with the host material and then deposited at the same time.

Other dopant materials shall not specifically be restricted, and known compounds can be used. They can be selected from various compounds according to emission colors desired. To be specific, they include, for example, condensed ring derivatives such as phenanthrene, anthracene, pyrene, tetracene, pentacene, perylene, naphthopyrene, dibenzopyrene, rubrene and the like, benzoxazole derivatives, benzothiazole derivatives, benzimidazole derivatives, benzotriazole derivatives, oxazole derivatives, oxadiazole derivatives, thiazole derivatives, imidazole derivatives, thiadiazole derivatives, triazole derivatives, pyrazoline derivatives, stilbene derivatives, thiophene derivatives, tetraphenylbutadiene derivatives, cyclopentadiene derivatives, bisstyryl derivatives (JP H1-245087 A/1989) such as bisstyrylanthracene derivatives, distyrylbenzene derivatives and the like, bisstyrylarylene derivatives (JP H2-247278 A/1990), diazaindacene derivatives, furan derivatives, benzofuran derivatives, isobenzofuran derivatives such phenylisobenzofuran, dimesitylisobenzofuran, di(2-methylphenyl)isobenzofuran, di(2-trifluoromethylphenyl)isobenzofuran, phenylisobenzofuran and the like, dibenzofuran derivatives, coumarin derivatives such as 7-dialkylaminocoumarin derivatives, 7-piperidinocoumarin derivatives, 7-hydroxycoumarin derivatives, 7-methoxycoumarin derivatives, 7-acetoxycoumarin derivatives, 3-benzothiazolylcoumarin derivatives, 3-benzimidazolylcoumarin derivatives, 3-benzoxazolylcoumarin derivatives and the like, dicyanomethylenepyran derivatives, dicyanomethylenethiopyran derivatives, polymethine derivatives, cyanine derivatives, oxobenzanthracene derivatives, xanthene derivatives, rhodamine derivatives, fluorescein derivatives, pyrylium derivatives, carbostyryl derivatives, acridine derivatives, oxazine derivatives, phenylene oxide derivatives, quinacridone derivatives, quinazoline derivatives, pyrrolopyridine derivatives, ferropyridine derivatives, 1,2,5-thiadiazolopyrene derivatives, pyrromethene derivatives, perinone derivatives, pyrrolopyrrole derivatives, squarylium derivatives, violanthrone derivatives, phenazine derivatives, acridone derivatives, deazaflavin derivatives and the like.

To give the examples thereof by color of emission, the blue to bluish green dopant materials include aromatic hydrocarbon compounds and derivatives thereof such as naphthalene, anthracene, phenanthrene, pyrene, triphenylene, perylene, fluorene, indene and the like, aromatic heterocyclic compounds and derivatives thereof such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthylidine, quinoxaline, pyrrolopyridine, thioxanthene and the like, distyrylbenzene derivatives, tetraphenylbutadiene derivatives, stilbene derivatives, aldazine derivatives, coumarin derivatives, azole derivatives and metal complexes thereof such as imidazole, thiazole, thiadiazole, carbazole, oxazole, oxadiazole, triazole and the like and aromatic amine derivatives represented by N,N'-diphenyl-N,N'-di(3-methylphenyl)-4,4'-diphenyl-1,1'-diamine.

The green to yellow dopant materials include coumarin derivatives, phthalimide derivatives, naphthalimide derivatives, perinone derivatives, pyrrolopyrrole derivatives, cyclopentadiene derivatives, acridone derivatives, quinacridone derivatives, naphthacene derivatives (such as rubrene) and the like. Further, the suitable examples thereof include compounds obtained by introducing substituents which can shift wavelengths to a longer side such as aryl group(s), heteroaryl group(s), arylvinyl group(s), amino group(s), cyano group(s) and the like into the compounds given as the examples of the blue to bluish green dopant materials described above.

Further, the orange to red dopant materials include naphthalimide derivatives such as bis(diisopropylphenyl)perylene tetracarboxylic imide, perinone derivatives, rare earth complexes such as Eu complexes having acetylacetone, benzoylacetone and phenanthroline as ligands, 4-(dicyanomethylene)-2-methyl-6-(p-dimethylaminostyryl)-4H-pyran and analogous compounds thereof, metal phthalocyanine derivatives such as magnesium phthalocyanine, aluminum chlorophthalocyanine and the like, rhodamine derivatives, deazaflavin derivatives, coumarin derivatives, quinacridone derivatives, phenoxazine derivatives, oxazine derivatives, quinazoline derivatives, pyrrolopyridine derivatives, squarylium derivatives, violanthrone derivatives, phenazine derivatives, phenoxazone derivatives, thidiazolopyrene and the like. Further, the suitable examples thereof include compounds obtained by introducing substituents which can shift wavelengths to a longer side such as aryl group(s), heteroaryl group(s), arylvinyl group(s), amino group(s), cyano group(s) and the like into the compounds given as the examples of the blue to bluish green and green to yellow dopant materials described above. Further, the suitable examples thereof include phosphorescent metal complexes comprising iridium and platinum as central metals represented by tris(8-phenylpyridine)iridium (III).

Among the dopant materials described above, the dopant materials which are suited to the material for the emission layer according to the present invention are particularly preferably the benzofluorene compound represented by Formula (1'), perylene derivatives, borane derivatives, amine-containing styryl derivatives, aromatic amine derivatives, coumarin derivatives, pyran derivatives, iridium complexes or platinum complexes.

The perylene derivatives include, for example, 3,10-bis(2,6-dimethylphenyl)perylene, 3,10-bis(2,4,6-trimethylphenyl)perylene, 3,10-diphenylperylene, 3,4-diphenylperylene, 2,5,8,11-tetra-t-butylperylene, 3,4,9,10-tetraphenylperylene, 3-(1'-pyrenyl)-8,11-di(-t-butyl)perylene, 3-(9'-anthryl)-8,11-di(-t-butyl)perylene, 3,3'-bis(8,11-di(-t-butyl)perylenyl) and the like.

Further, perylene derivatives described in JP H11-97178 A/1999, JP H12-133457 A/2000, JP H12-26324 A/2000, JP H13-267079 A/2001, JP H13-267078 A/2001, JP H13-267076 A/2001, JP H12-34234 A/2000, JP H13-267075 A/2001, JP H13-217077 A/2001 and the like may be used as well.

The borane derivatives include, for example, 1,8-diphenyl-10-(dimesitylboryl)anthracene, 9-phenyl-10-(dimesitylboryl)anthracene, 4-(9'-anthryl)dimesitylborylnaphthalene, 4-(10'-phenyl-9'-anthryl)dimesitylborylnaphthalene, 9-(dimesitylboryl)anthracene, 9-(4'-biphenylyl-10-(dimesitylboryl)anthracene, 9-(4'-(N-carbazolyl)phenyl)-10-(dimesitylboryl)anthracene and the like.

Further, borane derivatives described in International Publication No. 2000/40586 pamphlet and the like may be used as well.

The amine-containing styryl derivatives include, for example, N,N,N',N'-tetra(4-biphenylyl)-4,4'-diaminostilbene, N,N,N',N'-tetra(1-naphthyl)-4,4'-diaminostilbene, N,N,N',N'-tetra(2-naphthyl)-4,4'-diaminostilbene, N,N'-di(2-naphthyl)-N,N'-diphenyl-4,4'-diaminostilbene, N,N'-di(9-phenanthryl)-N,N'-diphenyl-4,4'-diaminostilbene, 4,4'-bis[4"-bis(diphenylamino)styryl]-biphenyl, 1,4-bis[4'-bis(diphenylamino)styryl]-benzene, 2,7-bis[4'-bis(diphenylamino)styryl]-9,9-dimethylfluorene, 4,4'-bis(9-ethyl-3-carbazovinylene)-biphenyl, 4,4'-bis(9-phenyl-3-carbazovinylene)-biphenyl and the like.

Further, amine-containing styryl derivatives described in JP H15-347056 A/2003, JP H13-307884 A/2001 and the like may be used as well.

The aromatic amine derivatives include, for example, N,N,N,N-tetraphenylanthracene-9,10-diamine, 9,10-bis(4-diphenylamino-phenyl)anthracene, 9,10-bis(4-di(1-naphthylamino)phenyl)anthracene, 9,10-bis(4-di(2-naphthylamino)phenyl)anthracene, 10-di-p-tolylamino-9-(4-di-p-tolylamino-1-naphthyl)anthracene, 10-diphenylamino-9-(4-diphenylamino-1-naphthyl)anthracene, 10-diphenylamino-9-(6-diphenylamino-2-naphthyl)anthracene, [4-(4-diphenylamino-phenyl)naphthalene-1-yl]-diphenylamine, [4-(4-diphenylamino-phenyl)naphthalene-1-yl]-diphenylamine, [6-(4-diphenylamino-phenyl)naphthalene-2-yl]-diphenylamine, 4,4'-bis[4-diphenylaminonaphthalene-1-yl]biphenyl, 4,4'-bis[6-diphenylaminonaphthalene-2-yl]biphenyl, 4,4"-bis[4-diphenylaminonaphthalene-1-yl]-p-terphenyl, 4,4"-bis[6-diphenylaminonaphthalene-2-yl]-p-terphenyl and the like.

Further, aromatic amine derivatives described in JP H18-156888 A/2006 and the like may be used as well.

The coumarin derivatives include coumarin-6, coumarin-334 and the like.

Further, coumarin derivatives described in JP H16-43646 A/2004, JP H13-76876 A/2001, JP H6-298758 A/1994 and the like may be used as well.

The pyran derivatives include DCM and DCJTB shown below.

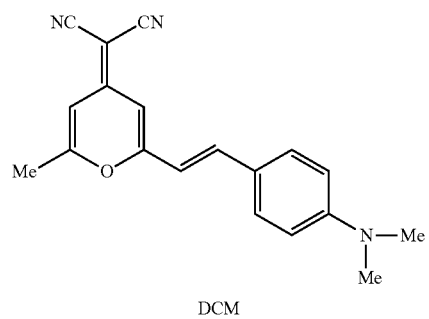

DCM

-continued

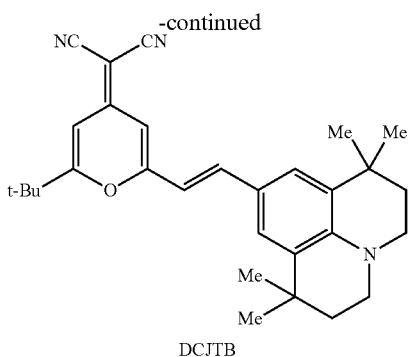

DCJTB

Further, pyran derivatives described in JP H17-126399 A/2005, JP H17-097283 A/2005, JP H14-234892 A/2002, JP H13-220577 A/2001, JP H13-081090 A/2001, JP H13-052869 A/2001 and the like may be used as well.

The iridium complexes include Ir(ppy)$_3$ shown below.

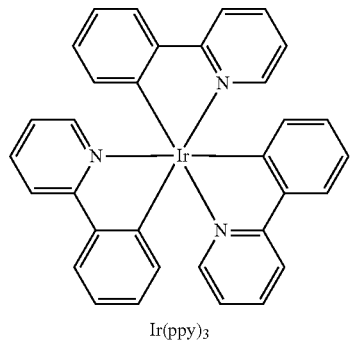

Ir(ppy)$_3$

Further, iridium complexes described in JP H18-089398 A/2005, JP H18-080419 A/2006, JP H17-298483 A/2005, JP H17-097263 A/2005, JP H16-111379 A/2004 and the like may be used as well.

The platinum complexes include PtOEP shown below.

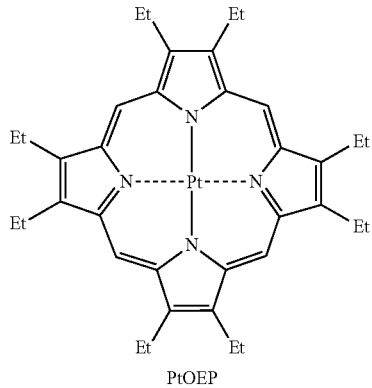

PtOEP

Further, platinum complexes described in JP H18-190718 A/2006, JP H18-128634 A/2006, JP H18-093542 A/2006, JP H16-335122 A/2004, JP H16-331508 A/2004 and the like may be used as well.

In addition to the compounds, compounds suitably selected from compounds described in Kagaku Kogyo (Chemical Industry) issued in June 2004 edition, p. 13 and references cited therein can be used as the dopant material.

<Electron Injection Layer and Electron Transport Layer in the Organic Electroluminescent Device>

The electron injection layer 107 plays a role of efficiently injecting electrons moving from the cathode 108 into the emission layer 105 or the electron transport layer 106. The electron transport layer 106 plays a role of efficiently transporting electrons injected from the cathode 108 or electrons injected from the cathode 108 via the electron injection layer 107 to the emission layer 105. The electron transport layer 106 and the electron injection layer 107 are formed respectively by laminating or mixing one or more electron transporting or injecting material(s) or from a mixture of the electron transporting or injecting material(s) with a high molecular binder.

An electron injection or transport layer is a layer into which electrons are injected from the cathode and which controls transportation of the electrons, and it is desirable that the electron injection efficiency is high and that the electrons injected are efficiently transported. Accordingly, preferred is the material which has large electron affinity and large electron mobility and is excellent in stability and in which impurities trapped are less liable to be generated in producing and using. However, when considering a transport balance between a hole and an electron, the material is provided, even if electron transport ability is not so high, with an effect of enhancing luminous efficiency to the same extent as that of a material having high electron transport ability in the case of playing principally a role of efficiently inhibiting holes coming from the anode from moving to a cathode side without recombination. Accordingly, the electron injection and transport layer in the present embodiment may be provided as well with a function of a layer which can efficiently inhibit holes from moving.

Compounds optionally selected from compounds which have so far been conventionally used as electron transport materials in photoconductive materials and publicly known compounds used for an electron injection layer and an electron transport layer of an organic electroluminescent device can be used as the materials used for the electron transport layer and the electron injection layer.

To be specific, the compounds include pyridine derivatives, naphthalene derivatives, anthracene derivatives, phenanthroline derivatives, perynone derivatives, coumarin derivatives, naphthalimide derivatives, anthraquinone derivatives, diphenoquinone derivatives, diphenylquinone derivatives, perylene derivatives, thiophene derivatives, thiadiazole derivatives, quinoxaline derivatives, polymers of quinoxaline derivatives, benzazole compounds, pyrazole derivatives, perfluorinated phenylene derivatives, triazine derivatives, pyrazine derivatives, imidazopyridine derivatives, borane derivatives, benzoxazole derivatives, benzothiazole derivatives, quinoline derivatives, aldazine derivatives, carbazole derivatives, indole derivatives, phosphorus oxide derivatives, bisstyryl derivatives and the like. Further, they include oxazole derivatives (1,3-bis[(4-t-butylphenyl)-1,3,4-oxadiazolyl]phenylene and the like), triazole derivatives (N-naphthyl-2,5-diphenyl-1,3,4-triazole and the like), benzoquinoline derivatives (2,2'-bis(benzo[h]quinoline-2-yl)-9,9'-spirobifluorene and the like), benzimidazole derivatives (tris(N-phenylbenzimidazole-2-yl)benzene and the like), bipyridine derivatives, terpyridine derivatives (1,3-bis(4'-(2,2':6',2"-terpyridinyl))benzene and the like), naphthyridine derivatives (bis(1-naphthyl)-4-(1,8-naphthyridine-2-yl)pheylphosphine oxide and the like) and the like. The materials may be used alone or in a mixture with different materials.

Further, metal complexes having electron accepting nitrogen can be used as well and include, for example, quinolinol metal complexes, hydroxyazole complexes such as hydroxyphenyloxazole complexes, azomethine complexes, tropolone metal complexes, flavonol metal complexes, benzoquinoline metal complexes and the like. The materials may be used alone or in a mixture with different materials.

Among the compounds, the quinolinol metal complexes, the pyridine derivatives or the phenanthroline derivatives are preferred.

The quinolinol metal complexes are compounds represented by Formula (E-1) shown below:

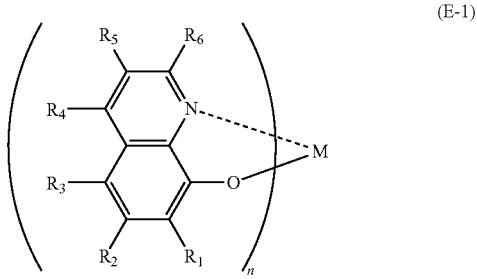

wherein $R_1$ to $R_6$ are hydrogen or a substituent; M is Al, Ga, Be or Zn; and n is an integer of 2 or 3.

The specific examples of the quinolinol metal complexes include tris(8-quinolinolate) aluminum (hereinafter abbreviated as ALQ), tris(4-methyl-8-quinolinolate)aluminum, tris(5-methyl-8-quinolinolate)aluminum, tris(3,4-dimethyl-8-quinolinolate)aluminum, tris(4,5-dimethyl-8-quinolinolate) aluminum, tris(4,6-dimethyl-8-quinolinolate)aluminum, bis(2-methyl-8-quinolinolate) (phenolate)aluminum, bis(2-methyl-8-quinolinolate) (2-methylphenolate)aluminum, bis(2-methyl-8-quinolinolate) (3-methylphenolate)aluminum, bis(2-methyl-8-quinolinolate) (4-methylphenolate)aluminum, bis(2-methyl-8-quinolinolate) (2-phenylphenolate)aluminum, bis(2-methyl-8-quinolinolate) (3-phenylphenolate) aluminum, bis(2-methyl-8-quinolinolate) (4-phenylphenolate)aluminum, bis(2-methyl-8-quinolinolate) (2,3-dimethylphenolate)aluminum, bis(2-methyl-8-quinolinolate) (2,6-dimethylphenolate)aluminum, bis(2-methyl-8-quinolinolate) (3,4-dimethylphenolate)aluminum, bis(2-methyl-8-quinolinolate) (3,5-dimethylphenolate) aluminum, bis(2-methyl-8-quinolinolate) (3,5-di-t-butylphenolate)aluminum, bis(2-methyl-8-quinolinolate) (2,6-diphenylphenolate)aluminum, bis(2-methyl-8-quinolinolate) (2,4,6-triphenylphenolate)aluminum, bis(2-methyl-8-quinolinolate) (2,4,6-trimethylphenolate)aluminum, bis(2-methyl-8-quinolinolate) (2,4,5,6-tetramethylphenolate) aluminum, bis(2-methyl-8-quinolinolate) (1-naphtholate) aluminum, bis(2-methyl-8-quinolinolate) (2-naphtholate) aluminum, bis(2,4-dimethyl-8-quinolinolate) (2-phenylphenolate)aluminum, bis(2,4-dimethyl-8-quinolinolate) (3-phenylphenolate)aluminum, bis(2,4-dimethyl-8-quinolinolate) (4-phenylphenolate)aluminum, bis(2,4-dimethyl-8-quinolinolate) (3,5-dimethylphenolate)aluminum, bis(2,4-dimethyl-8-quinolinolate) (3,5-di-t-butylphenolate) aluminum, bis(2-methyl-8-quinolinolate)aluminum-µ-oxo-bis(2-methyl-8-quinolinolate)aluminum, bis(2,4-dimethyl-8-quinolinolate)aluminum-µ-oxo-bis(2,4-dimethyl-8-quinolinolate) aluminum, bis(2-methyl-4-ethyl-8-quinolinolate)aluminum-µ-oxo-bis(2-methyl-4-ethyl-8-quinolinolate) aluminum, bis(2-methyl-4-methoxy-8-quinolinolate)aluminum-µ-oxo-bis(2-methyl-4-methoxy-8-quinolinolate)aluminum, bis(2-methyl-5-cyano-8-quinolinolate)aluminum-µ-oxo-bis(2-methyl-5-cyano-8-quinolinolate) aluminum, bis(2-methyl-5-trifluoromethyl-8-quinolinolate)aluminum-µ-oxo-bis(2-methyl-5-trifluoromethyl-8-quinolinolate)aluminum, bis(10-hydroxybenzo[h]quinoline)beryllium and the like.

The pyridine derivatives are compounds represented by Formula (E-2-1) or (E-2-2) shown below:

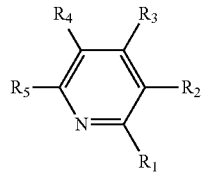

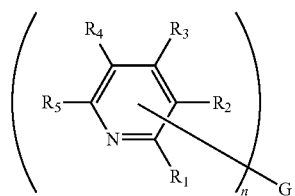

wherein $R_1$ to $R_5$ are hydrogen or a substituent, and the adjacent groups may be combined with each other to form condensed ring(s); G represents a mere bond or an n-valent linkage group; and n is an integer of 2 to 8.

G in Formula (E-2-2) includes, for example, groups shown by the following structural formulas. R(s) in the following structural formulas each are independently hydrogen, methyl, ethyl, isopropyl, cyclohexyl, phenyl, 1-naphthyl or 2-naphthyl.

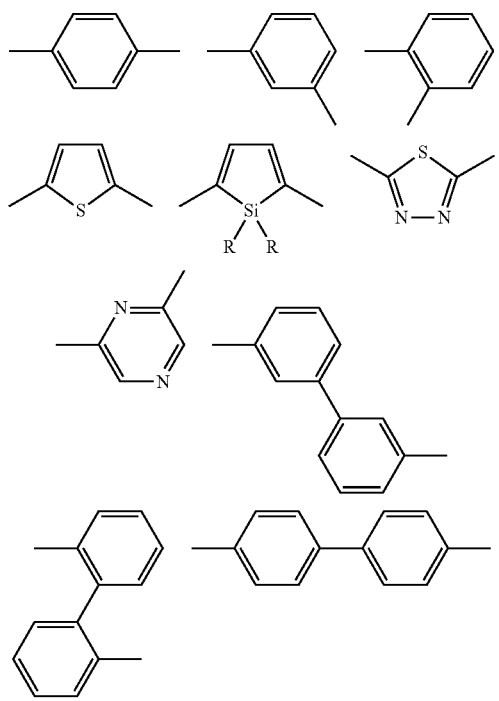

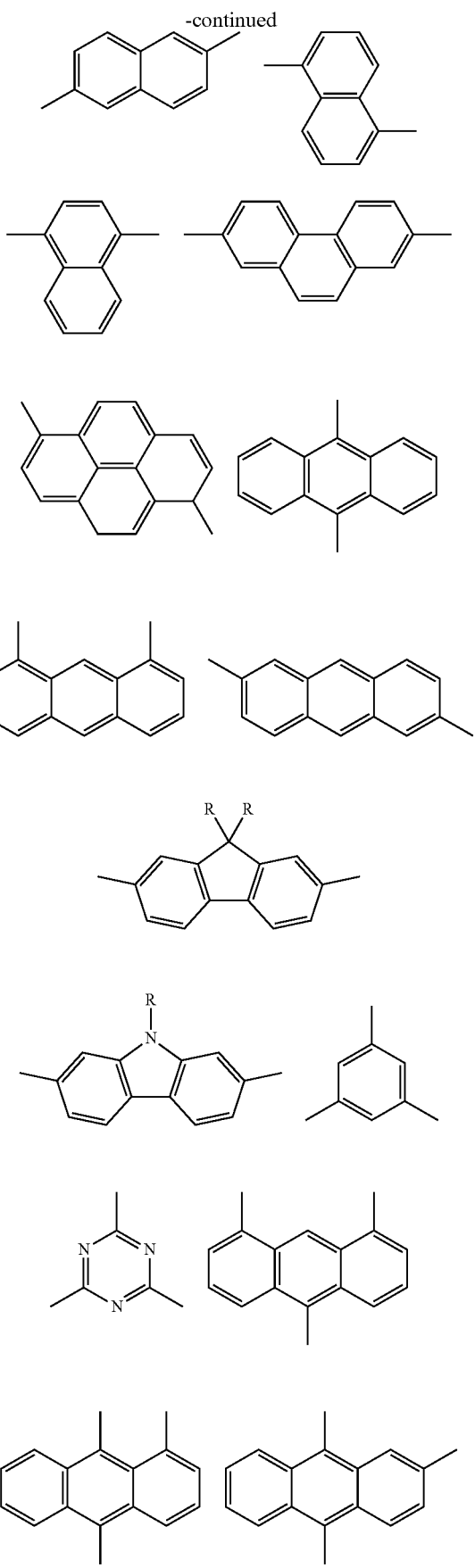

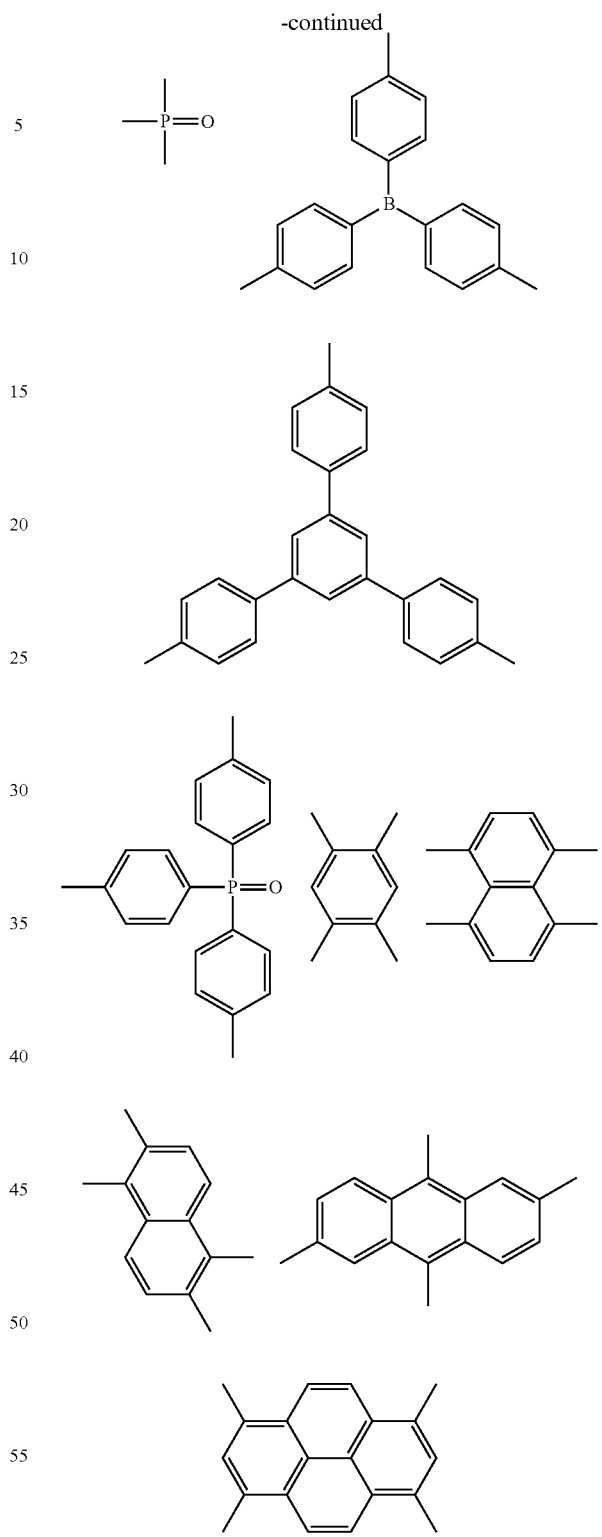

The specific examples of the pyridine derivative include, for example, 2,5-bis(2,2'-bipyridyl-6-yl)-1,1-dimethyl-3,4-diphenylsilole, 2,5-bis(2,2'-bipyridyl-6-yl)-1,1-dimethyl-3,4-dimesitylsilole (hereinafter abbreviated as ET1), 9,10-di(2,2'-bipyridyl-6-yl)anthracene, 9,10-di(2,2'-bipyridyl-5-yl)anthracene, 9,10-di(2,3'-bipyridyl-6-yl)anthracene, 9,10-di(2,3'-bipyridyl-5-yl)-2-phenylanthracene, 9,10-di(2,2'-bipyridyl-5-yl)-2-phenylanthracene, 3,4-diphenyl-2,5-di(2, 2'-bipyridyl-6-yl)thiophene, 3,4-diphenyl-2,5-di(2,3'-bipyridyl-5-yl)thiophene, 6',6"-di(2-pyridyl)-2,2':4',4":2":2"-quaterpyridine and the like.

The phenanthroline derivatives are compounds represented by Formula (E-3-1) or (E-3-2) shown below:

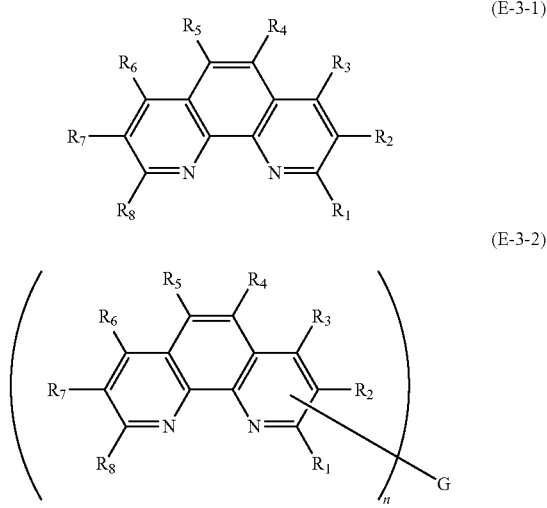

wherein $R_1$ to $R_5$ are hydrogen or a substituent, and the adjacent groups may be combined with each other to form condensed ring(s); G represents a mere bond or an n-valent linkage group; and n is an integer of 2 to 8. G in Formula (E-3-2) includes, for example, the same groups as explained in the column of the pyridine derivatives.

The specific examples of the phenanthroline derivative include 4,7-diphenyl-1,10-phenanthroline, 2,9-dimethyl-4,7-diphenyl-1,10-phenanthroline, 9,10-di(1,10-phenanthroline-2-yl)anthracene, 2,6-di(1,10-phenanthroline-5-yl)pyridine, 1,3,5-tri(1,10-phenanthroline-5-yl)benzene, 9,9'-difluoro-bis(1,10-phenanthroline-5-yl), bathocuproine, 1,3-bis(2-phenyl-1,10-phenanthroline-9-yl)benzene and the like.

In particular, a case where the phenanthroline derivative is used for the electron transport layer or the electron injection layer shall be explained. Materials which are excellent in thermal stability and thin film forming property are desired in order to obtain stable light emitting for a long time, and among the phenanthroline derivatives, preferred are compounds in which a substituent itself has a three-dimensional steric structure, compounds having a three-dimensional steric structure due to steric repulsion against a phenanthroline skeleton or an adjacent substituent and compounds obtained by linking plural phenanthroline skeletons. Further, in the case of the compounds obtained by linking plural phenanthroline skeletons, more preferred are the compounds containing a conjugate bond, substituted or non-substituted aromatic hydrocarbon or substituted or non-substituted aromatic heterocycle in a linkage unit.

<Cathode in the Organic Electroluminescent Device>

The cathode 108 plays a role of injecting electrons into the emission layer 105 via the electron injection layer 107 and the electron transport layer 106.

A material for forming the cathode 108 shall not specifically be restricted as long as it is a material which can efficiently inject electrons into the organic layers, and the same materials as the materials for forming the anode 102 can be used. Among them, preferred are metals such as tin, magnesium, indium, calcium, aluminum, silver, copper, nickel, chromium, gold, platinum, iron, zinc, lithium, sodium, potassium, and cesium and alloys thereof (magnesium-silver alloys, magnesium-indium alloys and aluminum-lithium alloys such as lithium fluoride/aluminum alloys) and the like. Lithium, sodium, potassium, cesium, calcium, magnesium and alloys containing the metals having a low work function are effective for elevating the electron injection efficiency to enhance the device characteristics. However, the metals having a low work function are usually instable in the air in many cases. In order to solve this issue a method in which a small amount of lithium, cesium or magnesium is doped in an organic layer to use an electrode having high stability is known. As other dopants, inorganic salts such as lithium fluoride, cesium fluoride, lithium oxide and cesium oxide can be used as well. However, it shall not be restricted to the materials.

Further, a preferred example for protecting the electrodes includes lamination of metals such as platinum, gold, silver, copper, iron, tin, aluminum and indium, alloys using these metals, inorganic substances such as silica, titania and silicon nitride, polyvinyl alcohol, polyvinyl chloride, hydrocarbon high molecular compounds and the like. A method for preparing the electrodes shall not specifically be restricted as long as the electrodes can conduct electricity and comprises resistance heating, electron beam, sputtering, ion plating, coating and the like.

<Binder which May be Used in the Respective Layers>

The materials used for the hole injection layer, the hole transport layer, the emission layer, the electron transport layer and the electron injection layer each described above can form alone the respective layers, and the materials which are dispersed in solvent-soluble resins such as polyvinyl chloride, polycarbonate, polystyrene, poly(N-vinylcarbazole), polymethyl methacrylate, polybutyl methacrylate, polyester, polysulfone, polyphenylene oxide, polybutadiene, hydrocarbon resins, ketone resins, phenoxy resins, polysulfone, polyamide, ethyl cellulose, vinyl acetate resins, ABS resins and polyurethane resins; curing resins such as phenol resins, xylene resins, petroleum resins, urea resins, melamine resins, unsaturated polyester resins, alkyd resins, epoxy resins and silicon resins; and the like as high molecular binders can be used as well.

<Preparing Method for the Organic Electroluminescent Device>

The respective layers constituting the organic electroluminescent device can be formed by forming thin films from the materials for constituting the respective layers by methods such as a vapor deposition method, resistance heating deposition, electron beam deposition, sputtering, a molecular lamination method, a printing method, a spin cast method, a cast method and a coating method. The film thicknesses of the respective layers thus formed shall not specifically be restricted and can suitably be set according to the properties of the materials, and they fall usually in a range of 2 nm to 5000 nm. The film thickness can usually be measured by means of a quartz oscillation type film thickness measuring apparatus and the like. When a thin film is formed by a deposition method, deposition conditions thereof are varied depending on the kind of the materials, the crystal structure and the aggregate structure which are aimed by the film, and the like. In general, the deposition conditions can suitably be set preferably in the ranges of a boat heating temperature of 50 to 400° C., a vacuum degree of $10^{-6}$ to $10^{-3}$ Pa, a deposition rate of 0.01 to 50 nm/second, a substrate temperature of −150 to +300° C. and a film thickness of 2 nm to 5 µm.

Next, a preparing method for an organic electroluminescent device comprising an anode/a hole injection layer/a hole transport layer/an emission layer comprising a host material and a dopant material/an electron transport layer/an electron injection layer/a cathode shall be explained as one example of a preparing method for the organic electroluminescent device. A thin film of an anode material is formed on a suitable substrate by a vapor deposition method and the like to prepare an anode, and then the thin films of a hole injection layer and a hole transport layer are formed on the anode. A host material and a dopant material are co-deposited thereon to form a thin film, whereby an emission layer is prepared, and an electron transport layer and an electron injection layer are formed on the emission layer. Further, a thin film comprising a substance for a cathode is formed thereon by a vapor deposition method and the like to prepare a cathode, whereby the targeted organic electroluminescent device is obtained. In preparing the organic electroluminescent device described above, the preparing order can be turned upside down to prepare it as well in the order of the cathode, the electron injection layer, the electron transport layer, the emission layer, the hole transport layer, the hole injection layer and the anode.

When direct voltage is applied to the organic electroluminescent device thus obtained, it may be applied with the anode being set to a polarity of + and the cathode being set to a polarity of −, and when a voltage of 2 to 40 V is applied, emission can be observed from a transparent or translucent electrode side (the anode or the cathode and both). This organic electroluminescent device emits light as well when applying a pulse current and an alternating current. A waveform of the alternating current applied may be optional.

<Application Examples of the Organic Electroluminescent Device>

The present invention can be applied as well to display units equipped with an organic electroluminescent device, lighting instruments equipped with an organic electroluminescent device and the like.

The display units or lighting instruments equipped with an organic electroluminescent device can be produced by such publicly known methods that the organic electroluminescent device according to the present embodiment is connected with publicly known drive apparatuses, and they can be driven by suitably using publicly known drive methods such as direct current drive, pulse drive, alternating current drive and the like.

The display unit includes, for example, panel displays such as color flat panel displays and flexible displays such as flexible color electroluminescent (EL) displays (refer to, for example, JP H10-335066 A/1998, JP H15-321546 A/2003, JP H16-281086 A/2004 and the like). A display system of the displays includes, for example, a matrix and/or segment display system and the like. A matrix display system and a segment display system may be coexistent in the same panel.

A matrix means a state in which pixels for display are two-dimensionally arranged in a lattice form, a mosaic form and the like, and characters and images are displayed by aggregate of the pixels. The form and the size of the pixels are determined by applications. For example, square pixels having a side of 300 µm or less are usually used for display of images and characters in personal computers, monitors and TV. In the case of a large-sized display such as display panels, pixels having a side of mm order are used. In the case of monochrome display, pixels having the same color are arranged, and in the case of color display, red, green and blue pixels are arranged for display. In this case, to be typical, a delta type and a stripe type are available. A drive method of this matrix may be either a linear sequential drive method or an active matrix. The linear sequential drive method has the advantage that it has a simpler structure. However, considering the operation characteristics, the active matrix is more excellent in a certain case, and therefore this has to be used separately depending on the applications.

In the segment system (type), patterns are formed so that informations determined in advance are displayed, and light is emitted in a determined area. It includes, for example, display of time and temperature in digital watches and thermometers, display of operation states in audio instruments and electromagnetic cookers and display of panels in automobiles.

The lighting instrument includes, for example, lighting instruments such as indoor lighting instruments, backlights for liquid crystal displays and the like (refer to, for example, JP H15-257621 A/2003, JP H15-277741 A/2003, JP H16-119211 A/2004 and the like). The backlights are used principally for a purpose of enhancing a visibility of display equipments which do not spontaneously emit light, and they are used for liquid crystal displays, watches, audio instruments, car panels, display boards, indicators and the like. In particular, considering that backlights of a conventional system for uses in liquid crystal displays, especially, personal computers in which a reduction in a size is a problem comprise fluorescent lumps and optical waveguides, so that it is difficult to reduce in a thickness thereof, a backlight using the light emitting device according to the present embodiment is characterized by that it is reduced in a thickness and has a light-weight.

<Synthetic Example of Benzofluorene Compound>

Next, the physical property values of some of the benzofluorene compounds synthesized are shown in Table 1. The respective physical property values are measured by the following methods. The glass transition temperatures which are guideposts for the melting points and the heat resistances were measured by means of Diamond DSC manufactured by Perkin Elmer Co., Ltd. (measuring conditions: cooling rate 200° C./minute, heating rate 10° C./minute). The UV absorption wavelengths were measured by means of a V-560 type spectrophotometer manufactured by JASCO Corporation, in which an excitation wavelength was set to 254 nm.

TABLE 1

| Compound | Melting point (° C.) | Tg (° C.) | UV absorption wavelength maximum value (nm) (MeOH) | Solubility (25° C.) g/100 ml (ethyl acetate) | Solubility (25° C.) g/100 ml (toluene) |
|---|---|---|---|---|---|
| Compound (1-13) | 270 | 151 | 360 | 1 | 8 |
| Compound (1-4) | 318 | 155 | 360 | — | — |
| Compound (2) | 301 | 140 | 349 | 0.2 | 0.9 |
| Compound (3) | 61 | 53 | 360 | — | — |
| Compound (4) | 64 | 54 | 348 | — | — |

TABLE 1-continued

| Compound | Melting point (° C.) | Tg (° C.) | UV absorption wavelength maximum value (nm) (MeOH) | Solubility (25° C.) g/100 ml (ethyl acetate) | Solubility (25° C.) g/100 ml (toluene) |
|---|---|---|---|---|---|
| Compound (1'-1) | 284.9 | 129.2 | 406 | — | — |
| Compound (1'-15) | — | — | 392 | — | — |

It can be found from the above-mentioned results that the glass transition temperatures of the compound (1-13) and the compound (1-4) are apparently higher than those of the compound (2), (3) and (4). The compound (1-13) and the compound (1-4) have higher glass transition temperature than those of the compounds (3) and (4), because substitution with alkyl in a five-membered ring of the benzofluorene skeleton provides the lower glass transition temperature than in substitution with aryl such as phenyl. The same tendency shall be observed in the case of the compound (1'-1) in which a substituent on a five-membered ring of the benzofluorene skeleton is phenyl.

Further, it can be found that the compound (1-13) is apparently more excellent in solubility in the solvents than the compound (2). This is considered to be attributed to the fact that the compound (1-13) has a benzo[c] skeleton. It is estimated that the same tendency shall be observed in the case of the compound (1-4) and the compound (1'-1) having the benzo[c] skeleton.

In Table 1, the benzofluorene compounds according to the present invention are only the compound (1-13), the compound (1-4), the compound (1'-1) and the compound (1'-15) in which $Ar^1$ and $Ar^2$ in Formula (1) described above are phenyl, and when the compounds in which $Ar^1$ and $Ar^2$ are, for example, biphenylyl are applied to a light emitting device, they have the same performances as those of the compound (1-13), the compound (1-4), the compound (1'-1) and the compound (1'-15). Also, the compound (1-13) is the compound in which $R^1$ and $R^2$ in Formula (1) described above are 2-naphthyl, and when all the compounds in which $R^1$ and $R^2$ are suitably selected from, for example, phenyl, biphenylyl, terphenylyl, quaterphenylyl, naphthyl and phenanthryl are applied to a light emitting device, they have the same performances as that of the compound (1-13). As a result of further experiment, when the compound (1-4), for example, in which $R^1$ and $R^2$ are selected from biphenylyl is applied to a light emitting device, it has the same performances as that of the compound (1-13). Further, the compound (1'-1) is the compound in which $R^1$ and $R^2$ in Formula (1') described above are N,N-diphenylamino, and when all the compounds in which $R^1$ and $R^2$ are suitably selected from, for example, N,N-di (biphenylyl)amino and N,N-dinaphthylamino are applied to a light emitting device, they have the same performances as that of the compound (1'-1). Also, the compound (1'-15) is the compound in which $R^1$ in Formula (1') described above is N,N-diphenylamino, and when all the compounds in which $R^1$ is suitably selected from, for example, N,N-di(biphenylyl) amino and N,N-dinaphthylamino are applied to a light emitting device, they have the same performances as that of the compound (1'-15).

The synthetic examples of the compound (1-13), the compound (1-4), the compound (2), the compound (3), the compound (4), the compound (1'-1) and the compound (1'-15) shall be explained below.

<Synthetic Example of the Compound (1-13)>

7,7-Diphenyl-5,9-bis(trifluoromethanesulfonyloxy)-7H-benzo[c]fluorene 6.66 g and 2-naphthyleneboronic acid 5.16 g were dissolved in 100 ml of a mixed solvent of tetrahydrofuran and isopropyl alcohol (tetrahydrofuran/isopropyl alcohol=1/4 (volume ratio)) under nitrogen atmosphere, and 1.16 g of tetrakis(triphenylphosphine)palladium (0) was added thereto, and the mixture was stirred for 5 minutes. Then, 12.7 g of potassium phosphate was added thereto, and the mixture was refluxed for 4 hours. After finishing the reaction, 50 ml of the solvent was removed. Water 100 ml was added thereto, and the precipitate was filtered. The precipitate was further washed with water and methanol to obtain a crude product of the compound (1-13). The crude product was subjected to column refining (solvent: heptane/toluene=3/1 (volume ratio)) with silica gel and then refined by sublimation to obtain 5.0 g of the targeted compound (1-13) (yield: 80.5%).

The structure of the compound (1-13) was confirmed by an MS spectrum and NMR measurement.

$^1$H-NMR (CDCl$_3$) δ=8.93 (d, 1H), 8.53 (d, 1H), 8.06 to 8.04 (m, 2H), 7.93 to 7.21 (m, 28H)

<Synthetic Example of the Compound (1-4)>

5,9-Dibrome-7,7-diphenyl-7H-benzo[c]fluorene 5.26 g and biphenyl boronic acid 4.36 g were dissolved in 50 ml of a mixed solvent of toluene and ethanol (toluene/ethanol=4/1 (volume ratio)) under nitrogen atmosphere, and 0.69 g of tetrakis(triphenylphosphine)palladium (0) was added thereto, and the mixture was stirred for 5 minutes. Then, 20 ml of 2M sodium hydrogencarbonate aqueous solution was added thereto, and the mixture was refluxed for 8 hours. After finishing the heating, the reaction mixture was cooled, and the organic layer was isolated and washed with saturated saline and then dried with anhydrous magnesium sulfate. Then, the desiccant agent was removed and the solvent was distilled away under reduced pressure to obtain a solid material. The solid material was subjected to column refining (solvent: heptane/toluene=3/1 (volume ratio)) with silica gel and then refined by sublimation to obtain 3.9 g of the targeted compound (1-4) (yield: 58%).

The structure of the compound (1-4) was confirmed by an MS spectrum and NMR measurement.

$^1$H-NMR (CDCl$_3$) δ=8.91 (d, 1H), 8.49 (d, 1H), 8.11 (d, 1H), 7.79 to 7.77 (m, 2H), 7.73 to 7.20 (m, 31H)

<Synthetic Example of the Compound (2)>

Synthesis of 3,9-dinaphthalene-2-yl-11,11-diphenyl-11H-benzo[a]fluorene was carried out by the following method.

11,11-Diphenyl-3,9-bis(trifluoromethanesulfonyloxy)-11H-benzo[a]fluorene 6.66 g and 2-naphthyleneboronic acid 5.16 g were dissolved in 100 ml of a mixed solvent of tetrahydrofuran and isopropyl alcohol (tetrahydrofuran/isopropyl alcohol=1/4 (volume ratio)) under nitrogen atmosphere, and 1.16 g of tetrakis(triphenylphosphine)palladium (0) was added thereto, and the mixture was stirred for 5 minutes. Then, 12.7 g of potassium phosphate was added thereto, and the mixture was refluxed for 4 hours. After finishing the reaction, 50 ml of the solvent was removed. Water 100 ml was added thereto, and the precipitate was filtered. The precipitate was further washed with water and methanol to obtain a crude product of the compound (2). The crude product was subjected to column refining (solvent: heptane/toluene=3/1 (volume ratio)) with silica gel and then refined by sublimation to obtain 4.2 g of the targeted compound (2) (yield: 67.6%).

The structure of the compound (2) was confirmed by an MS spectrum and NMR measurement.

$^1$H-NMR (CDCl$_3$) δ=8.23 (d, 1H), 8.1 to 8.08 (m, 3H), 7.98 to 7.67 (m, 14H), 7.51 to 7.42 (m, 8H), 7.27 to 7.22 (m, 6H)

<Synthetic Example of the Compound (3)>

Synthesis of 7,7-Dihexyl-5,9-di-naphthalene-2-yl-7H-benzo[c]fluorene was carried out by the following method.

5,9-Dibromo-7,7-dihexyl-7H-benzo[c]fluorene 5.42 g and 2-naphtylene boronic acid 3.78 g were dissolved in 50 ml of a mixed solvent of toluene and ethanol (toluene/ethanol=4/1 (volume ratio)) under nitrogen atmosphere, and 0.69 g of tetrakis(triphenylphosphine)palladium (0) was added thereto, and the mixture was stirred for 5 minutes. Then, 20 ml of 2M sodium hydrogencarbonate aqueous solution was added thereto, and the mixture was refluxed for 7 hours. After finishing the heating, the reaction mixture was cooled, and the organic layer was isolated and washed with saturated saline and then dried with anhydrous magnesium sulfate. Then, the desiccant agent was removed and the solvent was distilled away under reduced pressure to obtain a crude product. The crude product was subjected to column refining (solvent: heptane/toluene=3/1 (volume ratio)) with silica gel and then refined by sublimation to obtain 4.4 g of the targeted compound (3) (yield: 69%).

The structure of the compound (3) was confirmed by an MS spectrum and NMR measurement.

$^1$H-NMR (CDCl$_3$) δ=8.89 (d, 1H), 8.46 (d, 1H), 8.17 to 7.25 (m, 20H), 2.20 to 2.10 (m, 4H), 1.14 to 1.00 (m, 12H), 0.76 to 0.69 (m, 10H)

<Synthetic Example of the Compound (4)>

Synthesis of 11,11-Dihexyl-3,9-di-naphthalene-2-yl-11H-benzo[a]fluorene was carried out by the following method.

11,11-Dihexyl-3,9-bis(trifluoromethanesulfonyloxy)-11H-benzo[a]fluorene 6.81 g and 2-naphthyleneboronic acid 4.13 g were dissolved in 100 ml of a mixed solvent of tetrahydrofuran and isopropyl alcohol (tetrahydrofuran/isopropyl alcohol=1/4 (volume ratio)) under nitrogen atmosphere, and 1.16 g of tetrakis(triphenylphosphine)palladium (0) was added thereto, and the mixture was stirred for 5 minutes. Then, 12.7 g of potassium phosphate was added thereto, and the mixture was refluxed for 5 hours. After finishing the reaction, 50 ml of the solvent was removed. Water 100 ml was added thereto, and the precipitate was filtered. The precipitate was further washed with water and methanol to obtain a crude product of the compound (4). The crude product was subjected to column refining (solvent: heptane/toluene=5/1 (volume ratio)) with silica gel and then refined by sublimation to obtain 5.1 g of the targeted compound (4) (yield: 80%).

The structure of the compound (4) was confirmed by an MS spectrum and NMR measurement.

$^1$H-NMR (CDCl$_3$) δ=8.34 (d, 1H), 8.31 (d, 1H), 8.23 (d, 1H), 8.15 (d, 1H), 8.01 to 7.87 (m, 12H), 7.80 to 7.77 (m, 2H), 7.56 to 7.49 (m, 4H), 2.60 to 2.33 (m, 4H), 1.03 to 0.93 (m, 12H), 0.71 to 0.68 (t, 6H), 0.60 to 0.48 (m, 4H)

<Synthetic Example of the Compound (1'-1)>

5,9-Dibromo-7,7-diphenyl-7H-benzo[c]fluorene 2.5 g and diphenylamine 1.6 g were dissolved in 100 ml of dehydrated xylene under nitrogen atmosphere, and palladium acetate 1.5 mg, sodium t-butoxide 0.98 g and tri(t-butyl)phosphine 14 mg was added thereto and refluxed for 4 hours. After finishing the reaction, water 100 ml was added thereto, and the organic layer was washed with water in a separating funnel. The aqueous layer was removed, and then the organic layers were put together and concentrated by means of a rotary evaporator to obtain a crude product. The crude product was subjected to column refining (solvent: heptane/toluene=3/1 (volume ratio)) with silica gel and then refined by sublimation to obtain 450 mg of the targeted compound (1'-1) (yield: 13%).

The structure of the compound (1'-1) was confirmed by an MS spectrum and NMR measurement.

$^1$H-NMR (CDCl$_3$) δ=8.70 (d, 1H), 8.16 (d, 1H), 8.02 (d, 1H), 7.56 (t, 1H), 7.37 to 7.34 (m, 2H), 7.58 to 6.86 (m, 32H)

<Synthetic Example of the Compound (1'-15)>

5-Bromo-9-phenyl-7,7-diphenyl-7H-benzo[c]fluorene 1.4 g and diphenylamine 0.5 g were dissolved in 30 ml of dehydrated xylene under nitrogen atmosphere, and palladium acetate 3.0 mg, sodium t-butoxide 0.89 g and tri(t-butyl) phosphine 15 mg was added thereto and refluxed for 4 hours. After finishing the reaction, water 30 ml was added thereto, and the organic layer was washed with water in a separating funnel. The aqueous layer was removed, and then the organic layers were put together and concentrated by means of a rotary evaporator to obtain 1.1 g of the targeted compound (1'-15) (yield: 64%). The structure of the compound (1'-15) was confirmed by an MS spectrum.

The other benzofluorene compounds of the present invention can be synthesized according to the synthetic examples described above by suitably selecting the compounds of the raw materials.

EXAMPLES

Organic electroluminescent devices according to Examples 1, 2, 3, 4 and 5 and Comparative Example 1, 2, 3 and 4 were prepared to measure voltage (V) which is a characteristic in emission of 100 cd/m$^2$, current density (mA/cm$^2$), luminous efficiency (lm/W), current efficiency (cd/A), emission wavelength (nm), chromaticity (x, y), external quantum efficiency (%) and luminance retention rate (%) after 200 hours in an initial luminance of 1000 cd/m$^2$ or elapsed time at luminance retention rate 70% in an initial luminance of 2000 cd/m$^2$. Examples 1, 2, 3, 4 and 5 and Comparative Example 1, 2, 3 and 4 shall be explained below in details.

The material compositions of the respective layers in the organic electroluminescent devices prepared in Examples 1, 2, 3 and 4 and Comparative Example 1, 2 and 3 are shown in the following Table 2.

TABLE 2

| | Hole injection layer | Hole transport layer | Host | Dopant | Electron transport layer |
|---|---|---|---|---|---|
| Example 1 | CuPc | NPD | Compound 1-13 | D1 | ALQ |
| Example 2 | CuPc | NPD | Compound 1-13 | D1 | ET1 |
| Example 3 | CuPc | NPD | Compound 1-4 | D1 | ALQ |
| Example 4 | CuPc | NPD | Compound 1-4 | D1 | ET2 |
| Example 5 | CuPc | NPD | BH1 | Compound 1'-1 | ALQ |
| Comparative Example 1 | CuPc | NPD | Compound 2 | D1 | ALQ |
| Comparative Example 2 | CuPc | NPD | Compound 3 | D1 | ALQ |
| Comparative Example 3 | CuPc | NPD | Compound 3 | D1 | ET2 |
| Comparative Example 4 | CuPc | NPD | Compound 4 | D1 | ET2 |

In Table 2, Compound (1-13), Compound (1-4), Compound (1'-1), Compound (2), Compound (3) and Compound (4) each show Compound (1-13), Compound (1-4), Compound (1'-1), Compound (2), Compound (3) and Compound (4) in Table 1. In Table 2, CuPc is copper phthalocyanine; NPD is N,N'-di(1-naphthyl)-N,N'-diphenylbenzidine; D1 is N,N,N',N'-tetra(4-biphenylyl)-4,4-diaminostilbene; ALQ is tris(8-quinolinolate)aluminum; ET1 is 2,5-bis(2,2'-bipyridyl-6-yl)-1,1-dimethyl-3,4-dimesitylsilole; ET2 is 2,2',2"-(1,3,5-phenylene)tris(1-phenyl-1H-benzimidazole); and BH1 is 9-phenyl-10-(6-[1,1':3',1"]terphenyl-5'-yl-naphthalene-2-yl)-anthracene. They each have the following chemical structural formulas.

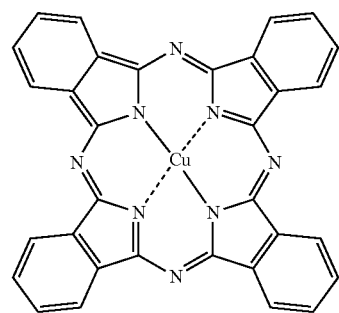

CuPc

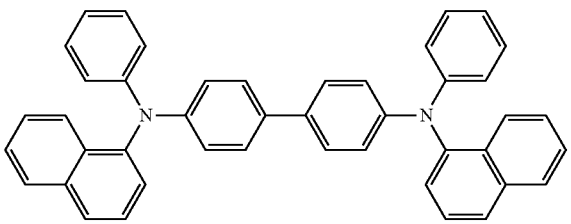

NPD

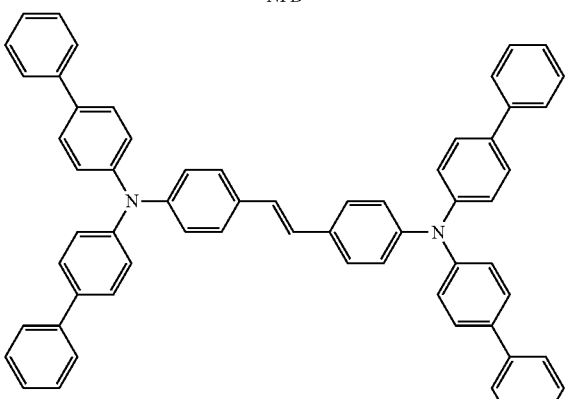

(D1)

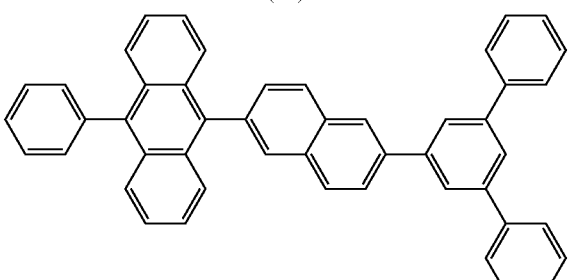

(BH1)

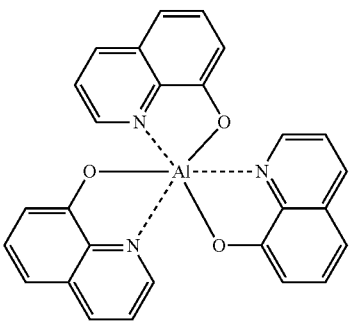

(ALQ)

-continued

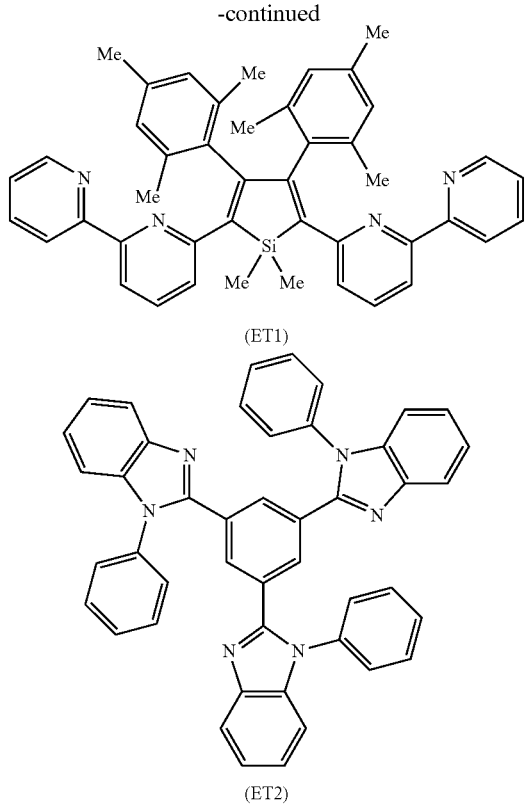

(ET1)

(ET2)

Example 1

A glass substrate of 26 mm×28 mm×0.7 mm on which ITO was deposited in a thickness of 150 nm was used as a transparent substrate. This transparent substrate was fixed on a substrate holder of a commercial deposition system, and loaded therein were a molybdenum-made boat for deposition containing CuPc, a molybdenum-made boat for deposition containing NPD, a molybdenum-made boat for deposition containing the compound (1-13), a molybdenum-made boat for deposition containing D1, a molybdenum-made boat for deposition containing ALQ, a molybdenum-made boat for deposition containing lithium fluoride and a tungsten-made boat for deposition containing Aluminum.

A vacuum chamber was reduced in pressure up to $5\times10^{-4}$ Pa, and the boat for deposition containing CuPc was heated to deposit it in a layer thickness of 20 nm, whereby a hole injection layer was formed. Then, the boat for deposition containing NPD was heated to deposit it in a layer thickness of 30 nm, whereby a hole transport layer was formed. Next, the molybdenum-made boat for deposition containing Compound (1-13) and the molybdenum-made boat for deposition containing D1 were heated to co-deposit both compounds in a layer thickness of 30 nm, whereby an emission layer was formed. In this regard, a doping concentration of D1 was about 5% by weight. Next, the boat for deposition containing ALQ was heated to deposit it in a layer thickness of 20 nm, whereby an electron transport layer was formed. The deposit rates of the layers described above were 0.01 to 1 nm/second.

Thereafter, the boat for deposition containing lithium fluoride was heated to deposit it at a deposition rate of 0.003 to 0.1 nm/second so that a layer thickness was 0.5 nm, and then the boat for deposition containing aluminum was heated to deposit it at a deposition rate of 0.01 to 10 nm/second so that a layer thickness was 100 nm, whereby an organic EL device was obtained.

With the ITO electrode set to an anode and the lithium fluoride/aluminum electrode set to a cathode, the characteristics in emission of 100 cd/m$^2$ were measured to find that the voltage was 4.8 V; the current density was 1.7 mA/cm$^2$; the luminous efficiency was 3.7 lm/W; the current efficiency was 5.7 cd/A; the emission wavelength was 455 nm; and the chromaticity was (0.145, 0.162). Further, the external quantum efficiency was 5.0%, and the current density in the external quantum efficiency was 10 mA/cm$^2$. A constant current operation test was carried out at current density for obtaining an initial luminance of 1000 cd/m$^2$ to find that the luminance retention rate was 89.0% after 200 hours passed.

Example 2

An organic EL device was obtained by a method according to Example 1, except that ALQ used for the electron transport layer in Example 1 was changed to ET1. With the ITO electrode set to an anode and the lithium fluoride/aluminum electrode set to a cathode, the characteristics in emission of 100 cd/m$^2$ were measured to find that the voltage was 3.7 V; the current density was 1.6 mA/cm$^2$; the luminous efficiency was 5.4 lm/W; the current efficiency was 6.3 cd/A; the emission wavelength was 455 nm; and the chromaticity was (0.145, 0.168). Further, the external quantum efficiency was 4.9%, and the current density in the external quantum efficiency was 10 mA/cm$^2$. The constant current operation test was carried out at current density for obtaining an initial luminance of 1000 cd/m$^2$ to find that the luminance retention rate was 76.2% after 200 hours passed.

Example 3

A glass substrate of 26 mm×28 mm×0.7 mm on which ITO was deposited in a thickness of 150 nm was used as a transparent substrate. This transparent substrate was fixed on a substrate holder of a commercial deposition system, and loaded therein were a molybdenum-made boat for deposition containing CuPc, a molybdenum-made boat for deposition containing NPD, a molybdenum-made boat for deposition containing the compound (1-4), a molybdenum-made boat for deposition containing D1, a molybdenum-made boat for deposition containing ALQ, a molybdenum-made boat for deposition containing lithium fluoride and a tungsten-made boat for deposition containing Aluminum.

A vacuum chamber was reduced in pressure up to $5\times10^{-4}$ Pa, and the boat for deposition containing CuPc was heated to deposit it in a layer thickness of 50 nm, whereby a hole injection layer was formed. Then, the boat for deposition containing NPD was heated to deposit it in a layer thickness of 30 nm, whereby a hole transport layer was formed. Next, the molybdenum-made boat for deposition containing Compound (1-4) and the molybdenum-made boat for deposition containing D1 were heated to co-deposit both compounds in a layer thickness of 35 nm, whereby an emission layer was formed. In this regard, a doping concentration of D1 was about 5% by weight. Next, the boat for deposition containing ALQ was heated to deposit it in a layer thickness of 15 nm, whereby an electron transport layer was formed. The deposit rates of the layers described above were 0.01 to 1 nm/second.

Thereafter, the boat for deposition containing lithium fluoride was heated to deposit it at a deposition rate of 0.003 to 0.1 nm/second so that a layer thickness was 0.5 nm, and then the boat for deposition containing aluminum was heated to deposit it at a deposition rate of 0.01 to 10 nm/second so that a layer thickness was 100 nm, whereby an organic EL device was obtained.

With the ITO electrode set to an anode and the lithium fluoride/aluminum electrode set to a cathode, the characteristics in emission of 100 cd/m² were measured to find that the voltage was 4.6 V; the current density was 1.9 mA/cm²; the luminous efficiency was 3.6 lm/W; the current efficiency was 5.3 cd/A; the emission wavelength was 455 nm; and the chromaticity was (0.141, 0.140). Further, the external quantum efficiency was 5.1%, and the current density in the external quantum efficiency was 2 mA/cm². A constant current operation test was carried out at current density for obtaining an initial luminance of 2000 cd/m² to find that the elapsed time at luminance retention rate 70% was 165 hours.

Example 4

An organic EL device was obtained by a method according to Example 3, except that ALQ used for the electron transport layer in Example 3 was changed to ET2. With the ITO electrode set to an anode and the lithium fluoride/aluminum electrode set to a cathode, the characteristics in emission of 100 cd/m² were measured to find that the voltage was 4.4 V; the current density was 1.8 mA/cm²; the luminous efficiency was 4.0 lm/W; the current efficiency was 5.6 cd/A; the emission wavelength was 455 nm; and the chromaticity was (0.141, 0.142). Further, the external quantum efficiency was 5.4%, and the current density in the external quantum efficiency was 2 mA/cm². The constant current operation test was carried out at current density for obtaining an initial luminance of 2000 cd/m² to find that the elapsed time at luminance retention rate 70% was 88 hours.

Example 5

An organic EL device was obtained by a method according to Example 1, except that the compound (1-13) used as the host in Example 1 was changed to BH1 and that D1 used as the dopant was changed to the compound (1'-1). With the ITO electrode set to an anode and the lithium fluoride/aluminum electrode set to a cathode, the characteristics in emission of 100 cd/m² were measured to find that the voltage was 5.3 V; the current density was 1.8 mA/cm²; the luminous efficiency was 3.3 lm/W; the current efficiency was 5.5 cd/A; the emission wavelength was 460 nm; and the chromaticity was (0.140, 0.159). Further, the external quantum efficiency was 5.2%, and the current density in the external quantum efficiency was 10 mA/cm². The constant current operation test was carried out at current density for obtaining an initial luminance of 1000 cd/m² to find that the luminance retention rate was 90.0% after 200 hours passed.

Comparative Example 1

An organic EL device was obtained by a method according to Example 1, except that the compound (1-13) used as the host in Example 1 was changed to the compound (2). With the ITO electrode set to an anode and the lithium fluoride/aluminum electrode set to a cathode, the characteristics in emission of 100 cd/m² were measured to find that the voltage was 5.2 V; the current density was 1.7 mA/cm²; the luminous efficiency was 3.5 lm/W; the current efficiency was 5.8 cd/A; the emission wavelength was 456 nm; and the chromaticity was (0.145, 0.168). Further, the external quantum efficiency was 4.8%, and the current density in the external quantum efficiency was 10 mA/cm². The constant current operation test was carried out at current density for obtaining an initial luminance of 1000 cd/m² to find that the luminance retention rate was 88.5% after 200 hours passed.

Comparative Example 2

An organic EL device was obtained by a method according to Example 3, except that the compound (1-4) used as the host in Example 3 was changed to the compound (3). With the ITO electrode set to an anode and the lithium fluoride/aluminum electrode set to a cathode, the characteristics in emission of 100 cd/m² were measured to find that the voltage was 5.3 V; the current density was 19.5 mA/cm²; the luminous efficiency was 0.31 lm/W; the current efficiency was 0.5 cd/A; the emission wavelength was 520 nm; and the chromaticity was (0.239, 0.523). Further, the external quantum efficiency was 0.2%, and the current density in the external quantum efficiency was 17.2 mA/cm². Also, the organic EL device has very low efficiency because it has ALQ luminescence.

Comparative Example 3

An organic EL device was obtained by a method according to Example 4, except that the compound (1-4) used as the host in Example 4 was changed to the compound (3). With the ITO electrode set to an anode and the lithium fluoride/aluminum electrode set to a cathode, the characteristics in emission of 100 cd/m² were measured to find that the voltage was 4.7 V; the current density was 2.6 mA/cm²; the luminous efficiency was 2.6 lm/W; the current efficiency was 3.8 cd/A; the emission wavelength was 450 nm; and the chromaticity was (0.142, 0.114). Further, the external quantum efficiency was 4.6%, and the current density in the external quantum efficiency was 3.2 mA/cm². The constant current operation test was carried out at current density for obtaining an initial luminance of 2000 cd/m² to find that the elapsed time at luminance retention rate 70% was 1 hour.

Comparative Example 4

An organic EL device was obtained by a method according to Example 4, except that the compound (1-4) used as the host in Example 4 was changed to the compound (4). With the ITO electrode set to an anode and the lithium fluoride/aluminum electrode set to a cathode, the characteristics in emission of 100 cd/m² were measured to find that the voltage was 4.8 V; the current density was 2.4 mA/cm²; the luminous efficiency was 2.7 lm/W; the current efficiency was 4.2 cd/A; the emission wavelength was 450 nm; and the chromaticity was (0.142, 0.120). Further, the external quantum efficiency was 4.7%, and the current density in the external quantum efficiency was 2.2 mA/cm². The constant current operation test was carried out at current density for obtaining an initial luminance of 2000 cd/m² to find that the elapsed time at luminance retention rate 70% was 29 hours.

The performance evaluation results of the organic electroluminescent devices prepared in Examples 1, 2, 3, 4 and 5 and Comparative Example 1, 2, 3 and 4 are summarized in the following Table 3.

TABLE 3

| | Characteristics in emission of 100 cd/m² | | | | | External quantum efficiency | | Life | |
|---|---|---|---|---|---|---|---|---|---|
| | | | | | | | | luminance retention rate after 200 hours passed (initial luminance: 1000 cd/m²) % | Elapsed time at luminance retention rate 70% (initial luminance: 2000 cd/m²) hour |
| | Voltage V | Current density mA/cm² | Luminous efficiency lm/W | Current efficiency cd/A | Emission wavelength nm | Chromaticity (x, y) | % | Current density mA/cm² | | |
| Ex. 1 | 4.8 | 1.7 | 3.7 | 5.7 | 455 | 0.145, 0.162 | 5.0 | 10 | 89.0 | — |
| Ex. 2 | 3.7 | 1.6 | 5.4 | 6.3 | 455 | 0.145, 0.168 | 4.9 | 10 | 76.2 | — |
| Ex. 3 | 4.6 | 1.9 | 3.6 | 5.3 | 455 | 0.141, 0.140 | 5.1 | 2 | — | 165 |
| Ex. 4 | 4.4 | 1.8 | 4.0 | 5.6 | 455 | 0.141, 0.142 | 5.4 | 2 | — | 88 |
| Ex. 5 | 5.3 | 1.8 | 3.3 | 5.5 | 460 | 0.140, 0.159 | 5.2 | 10 | 90.0 | — |
| Comp. Ex. 1 | 5.2 | 1.7 | 3.5 | 5.8 | 456 | 0.145, 0.168 | 4.8 | 10 | 88.5 | — |
| Comp. Ex. 2 | 5.3 | 19.5 | 0.3 | 0.5 | 520 | 0.239, 0.523 | 0.2 | 17.2 | — | — |
| Comp. Ex. 3 | 4.7 | 2.6 | 2.6 | 3.8 | 450 | 0.142, 0.114 | 4.6 | 3.2 | — | 1 |
| Comp. Ex. 4 | 4.8 | 2.4 | 2.7 | 4.2 | 450 | 0.140, 0.120 | 4.7 | 2.2 | — | 29 |

It can be found from the result of Comparative Examples 2, 3 and 4 that substitution with alkyl in a five-membered ring of the benzofluorene skeleton provides low luminous efficiency and current efficiency of the EL devices, and short life.

INDUSTRIAL APPLICABILITY

According to the preferred embodiment of the present invention, broader width in selecting the solvents in the synthesis makes it possible to enhance freedom in the synthesis of the compounds and employ free layer-forming means in forming the layers of the light emitting device. Further, capable of being provided are an organic electroluminescent device having better performances in at least one of heat resistance, luminous efficiency, current efficiency, device life and external quantum efficiency, a display unit equipped with the same, a lighting instrument equipped with the same and the like.

BRIEF EXPLANATION OF THE DRAWING

FIG. 1 is an outline cross-sectional drawing showing the organic electroluminescent device according to the present embodiment.

EXPLANATIONS OF CODES

100 Organic electroluminescent device
101 Substrate
102 Anode
103 Hole injection layer
104 Hole transport layer
105 Emission layer
106 Electron transport layer
107 Electron injection layer
108 Cathode

What is claimed is:

1. A benzofluorene compound represented by the following Formula (1):

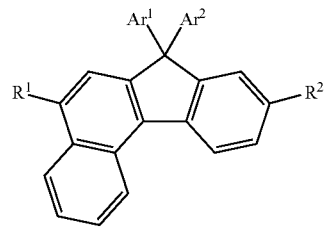

wherein $Ar^1$ and $Ar^2$ are aryl which may be substituted;
$R^1$ and $R^2$ each are independently hydrogen, alkyl which may be substituted, cycloalkyl which may be substituted or aryl which may be substituted, and at least one of $R^1$ and $R^2$ is aryl which may be substituted; and
the substituents in $Ar^1$, $Ar^2$, $R^1$ and $R^2$ each are independently selected from the group consisting of alkyl having 1 to 24 carbon atoms, cycloalkyl having 3 to 12 carbon atoms and aryl having 6 to 30 carbon atoms.

2. The benzofluorene compound according to claim 1, wherein $Ar^1$ and $Ar^2$ are aryl having 6 to 30 carbon atoms which may be substituted; and
$R^1$ and $R^2$ each are independently hydrogen, alkyl having 1 to 24 carbon atoms which may be substituted, cycloalkyl having 3 to 12 carbon atoms which may be substituted or aryl having 6 to 30 carbon atoms which may be substituted, and at least one of $R^1$ and $R^2$ is aryl having 6 to 30 carbon atoms which may be substituted.

3. The benzofluorene compound according to claim 1, wherein $Ar^1$ and $Ar^2$ are aryl having 6 to 16 carbon atoms which may be substituted;
$R^1$ and $R^2$ are aryl having 6 to 24 carbon atoms which may be substituted; and
the substituents in $Ar^1$, $Ar^2$, $R^1$ and $R^2$ each are independently selected from the group consisting of alkyl having 1 to 12 carbon atoms, cycloalkyl having 3 to 6 carbon atoms and aryl having 6 to 20 carbon atoms.

4. The benzofluorene compound according to claim 1, wherein $Ar^1$ and $Ar^2$ are aryl having 6 to 12 carbon atoms which may be substituted;

$R^1$ and $R^2$ are aryl having 6 to 20 carbon atoms which may be substituted; and the substituents in $Ar^1$, $Ar^2$, $R^1$ and $R^2$ each are independently selected from the group consisting of methyl, ethyl, propyl, t-butyl, cyclobutyl, cyclopentyl, cyclohexyl, phenyl, biphenylyl and naphthyl.

5. The benzofluorene compound according to claim 1, wherein $Ar^1$ and $Ar^2$ each are independently phenyl or biphenylyl; and $R^1$ and $R^2$ each are independently phenyl, biphenylyl, terphenylyl, quaterphenylyl, naphthyl or phenanthryl.

6. The benzofluorene compound according to claim 1, wherein $Ar^1$ and $Ar^2$ are aryl having 6 to 16 carbon atoms which may be substituted;

one of $R^1$ and $R^2$ is hydrogen, and the other is aryl having 6 to 24 carbon atoms which may be substituted; and the substituents in $Ar^1$, $Ar^2$, $R^1$ and $R^2$ each are independently selected from the group consisting of alkyl having 1 to 12 carbon atoms, cycloalkyl having 3 to 6 carbon atoms and aryl having 6 to 20 carbon atoms.

7. The benzofluorene compound according to claim 1, wherein $Ar^1$ and $Ar^2$ are aryl having 6 to 12 carbon atoms which may be substituted;

one of $R^1$ and $R^2$ is hydrogen, and the other is aryl having 6 to 20 carbon atoms which may be substituted; and the substituents in $Ar^1$, $Ar^2$, $R^1$ and $R^2$ each are independently selected from the group consisting of methyl, ethyl, propyl, t-butyl, cyclobutyl, cyclopentyl, cyclohexyl, phenyl, biphenylyl and naphthyl.

8. The benzofluorene compound according to claim 1, wherein $Ar^1$ and $Ar^2$ each are independently phenyl or biphenylyl; and one of $R^1$ and $R^2$ is hydrogen, and the other is phenyl, biphenylyl, terphenylyl, quaterphenylyl, naphthyl or phenanthryl.

9. The benzofluorene compound according to claim 1, wherein $Ar^1$ and $Ar^2$ are phenyl;

$R^1$ is 4-biphenylyl, and $R^2$ is 4-biphenylyl.

10. The benzofluorene compound according to claim 1, wherein $Ar^1$ and $Ar^2$ are phenyl;

$R^1$ is 2-naphthyl, and $R^2$ is 2-naphthyl.

11. The benzofluorene compound according to claim 1, wherein $Ar^1$ and $Ar^2$ are phenyl;

$R^1$ is 4-biphenylyl, and $R^2$ is 2-naphthyl.

12. The benzofluorene compound according to claim 1, wherein $Ar^1$ and $Ar^2$ are phenyl;

$R^1$ is 2-naphthyl, and $R^2$ is 4-biphenylyl.

13. A material for an emission layer in a light emitting device comprising the benzofluorene compound according to claim 1.

14. The material for an emission layer according to claim 13, further comprising at least one compound selected from the group consisting of a perylene derivative, a borane derivative, an amine-containing styryl derivative, an aromatic amine derivative, a coumarin derivative, a pyran derivative, an iridium complex and a platinum complex.

15. An organic electroluminescent device comprising a pair of electrodes comprising an anode and a cathode, and an emission layer which is disposed between the pair of the electrodes and comprising the material for an emission layer according to claim 13.

16. The organic electroluminescent device according to claim 15, further comprising an electron transport layer and/or an electron injection layer disposed between the cathode and the emission layer, wherein at least one of the electron transport layer and the electron injection layer comprises at least one compound selected from the group consisting of a quinolinol metal complex, a pyridine derivative and a phenanthroline derivative.

17. A display unit comprising the organic electroluminescent device according to claim 15.

18. A lighting instrument comprising the organic electroluminescent device according to claim 15.

19. The material for an emission layer according to claim 13, wherein the material for an emission layer is a host material.

* * * * *